United States Patent
Tsujita

(10) Patent No.: US 9,786,040 B2
(45) Date of Patent: Oct. 10, 2017

(54) ULTRASOUND DIAGNOSTIC APPARATUS AND ULTRASOUND TWO-DIMENSIONAL CROSS-SECTION IMAGE GENERATION METHOD

(71) Applicant: HITACHI, LTD., Chiyoda-ku, Tokyo (JP)

(72) Inventor: Takehiro Tsujita, Mitaka (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/431,603

(22) PCT Filed: Sep. 12, 2013

(86) PCT No.: PCT/JP2013/074721
§ 371 (c)(1),
(2) Date: Mar. 26, 2015

(87) PCT Pub. No.: WO2014/050596
PCT Pub. Date: Apr. 3, 2014

(65) Prior Publication Data
US 2015/0248750 A1 Sep. 3, 2015

(30) Foreign Application Priority Data
Sep. 26, 2012 (JP) .................. 2012-213184

(51) Int. Cl.
*G06T 7/00* (2017.01)
*A61B 8/08* (2006.01)
(Continued)

(52) U.S. Cl.
CPC .............. *G06T 7/00* (2013.01); *A61B 5/0059* (2013.01); *A61B 8/0883* (2013.01); *A61B 8/483* (2013.01);
(Continued)

(58) Field of Classification Search
CPC . G06T 2207/10081; G06T 2207/10116; G06T 11/003; G06T 2207/10132; G06T 11/00; G06T 5/008; G06T 7/00; A61B 8/0883; A61B 8/483; A61B 5/0059
See application file for complete search history.

(56) References Cited

U.S. PATENT DOCUMENTS

2004/0075658 A1 4/2004 Goto
2004/0077946 A1* 4/2004 Ohmiya .............. G01S 15/8995
600/437
(Continued)

FOREIGN PATENT DOCUMENTS

JP 2001-351120 A 12/2001
JP 2005-074227 A 3/2005
(Continued)

OTHER PUBLICATIONS

Oct. 8, 2013 International Search Report dated in International Application No. PCT/JP2013/074721.

*Primary Examiner* — Kenny Cese
(74) *Attorney, Agent, or Firm* — Oliff PLC

(57) ABSTRACT

An ultrasound diagnostic apparatus includes a light source information setting unit setting light source data indicating a property of a light source irradiated to a cross section region of the object, an optical property setting unit setting a weight coefficient indicating an optical property of cross-section region data including intensity information on the cross section region to the light source, an illuminance slice data creation unit calculating illuminance at positions corresponding to coordinates of a plurality of the cross-section regions based on the light source data and the weight coefficient, and creating illuminance slice data of the plurality of the cross-section regions based on the calculated illuminance, and a composition unit compositing a two-dimensional cross-section image of the object from the plurality of illuminance slice data.

9 Claims, 14 Drawing Sheets

(51) Int. Cl.
*A61B 5/00* (2006.01)
*G01S 15/89* (2006.01)

(52) U.S. Cl.
CPC ......... *G01S 15/899* (2013.01); *G01S 15/8993* (2013.01); *G06T 2207/10004* (2013.01); *G06T 2207/10132* (2013.01)

(56) References Cited

U.S. PATENT DOCUMENTS

| | | | |
|---|---|---|---|
| 2005/0264813 A1* | 12/2005 | Giakos | B82Y 20/00 356/369 |
| 2006/0071932 A1 | 4/2006 | Weese et al. | |
| 2007/0078343 A1* | 4/2007 | Kawashima | A61B 8/12 600/443 |
| 2009/0119808 A1* | 5/2009 | Giakos | B82Y 20/00 850/31 |
| 2011/0123077 A1 | 5/2011 | Goto | |
| 2012/0061590 A1* | 3/2012 | Khojasteh | A61B 1/0638 250/459.1 |
| 2013/0336551 A1* | 12/2013 | Clingman | G06T 7/0012 382/128 |

FOREIGN PATENT DOCUMENTS

| | | |
|---|---|---|
| JP | 2006-507051 A | 3/2006 |
| JP | 2008-259697 A | 10/2008 |
| JP | 2010-017490 A | 1/2010 |

\* cited by examiner

ULTRASOUND DIAGNOSTIC APPARATUS AND ULTRASOUND TWO-DIMENSIONAL CROSS-SECTION IMAGE GENERATION METHOD

TECHNICAL FIELD

The present invention relates to an ultrasound diagnostic apparatus, and particularly, to an ultrasound diagnostic apparatus that generates a two-dimensional cross-section image from intensity volume data of an ultrasonic wave.

BACKGROUND ART

An ultrasound diagnostic apparatus sends an ultrasonic wave to the inside of a diagnosing object by an ultrasound probe, receives a reflected echo signal which corresponds to a structure of a biological tissue from the inside of the diagnosing object, and forms a cross-section image, e.g., an ultrasonic cross-section image (B-mode image), or the like, to be displayed for a diagnosis.

In order to collect three-dimensional ultrasonic data, in the typical technique, three-dimensional data obtained by scanning a probe automatically or manually in a short axis direction is subject to coordinate conversion, thereafter ultrasonic image data is reconfigured in a visual line direction, and a three-dimensional image is created, thereby a surface of an object is observed. The recent typical technique is a technique called real-time 3D or 4D, in which signal processing described above is performed in real time, and a moving three-dimensional image is displayed.

Also, in order to observe not a surface but an arbitrary cross-section region of a three-dimensional space, or in order to obtain a detailed image, a typical technique is displaying an arbitrary cross-section region from three-dimensional data.

However, as in the case of a normal two-dimensional cross-section image, the aforementioned techniques have a problem that a diffraction pattern called speckle, which is unique to ultrasound, causes a break in display of regions, which is expected to be continued, or a problem that a three-dimensional structure of an object is not obvious.

Examples of a method for solving the aforementioned problems include a method disclosed in Patent Literature 1. It is disclosed that a technique is selected for rendering volume which is one of surface texture, maximum density, minimum density, average projection, rendering an inclined light, and maximum transparency, in order to display an emphasized C plane image by emphasizing one of the anatomical features.

CITATION LIST

Patent Literature

Patent Literature 1: JP-A-2005-74227

SUMMARY OF INVENTION

Technical Problem

In a conventional ultrasound diagnostic apparatus, however, unlike a macro specimen observed by a naked eye or a micro specimen observed by being exposed to light from the rear with a microscope or a loupe, it is impossible to obtain a cross-section image in which a structure can be clearly seen and reality is improved.

The present invention has been made to solve the conventional problems, and the object thereof is to provide an arbitrary cross-section image of a three-dimensional space with an optical property (or a shading effect) indicating a behavior of light (leakage, absorption, scattering, reflection, etc.) to obtain a cross-section image in which a structure can be clearly seen and reality is improved.

Solution to Problem

An ultrasound diagnostic apparatus of the present invention includes: a light source information setting unit configured to set a property of a light source irradiated to a cross section region of an object, the light source information setting unit generating light source data based on the property of the light source; an optical property setting unit configured to set a weight coefficient indicating an optical property of cross-section region data to the light source, the cross-section region data including intensity information on the cross section region; an illuminance slice data creation unit configured to calculate illuminance at a position corresponding to coordinates of a plurality of the cross section regions based on the light source data and the weight coefficient, and create illuminance slice data of the plurality of the cross section regions based on the calculated illuminance; and a composition unit configured to composite a two-dimensional cross-section image of the object from the plurality of the illuminance slice data.

According to this configuration, it is possible to provide an arbitrary cross-section image of a three-dimensional space with an optical property (or a shading effect) indicating a behavior of light (leakage, absorption, scattering, reflection, etc.) to obtain a cross-section image in which a structure can be clearly seen and reality is improved.

Advantageous Effects of Invention

The present invention enables providing an arbitrary cross-section image of a three-dimensional space with an optical property (or a shading effect) indicating a behavior of light (leakage, absorption, scattering, reflection, etc.) to obtain a cross-section image in which a structure can be clearly seen and reality is improved.

DESCRIPTION OF EMBODIMENT

Figure 1:
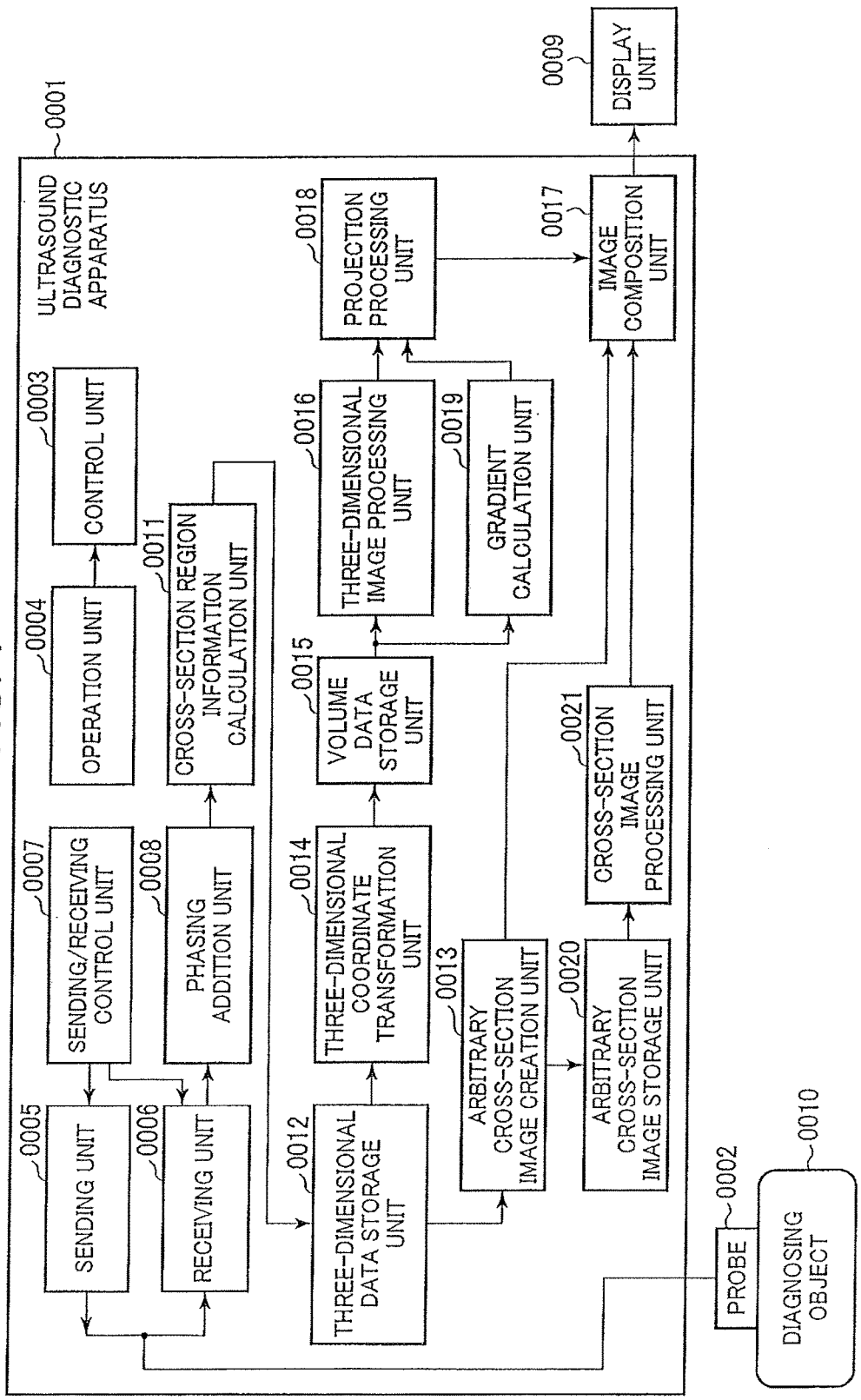
FIG. 1 is a block diagram illustrating an example of an ultrasound diagnostic apparatus according to a present embodiment.

Hereinafter, descriptions will be given of an ultrasound diagnostic apparatus of the present invention, using the drawings. FIG. 1 is a block diagram illustrating an example of an ultrasound diagnostic apparatus according to a present embodiment. As illustrated in FIG. 1, an ultrasound diagnostic apparatus 0001 includes a control unit 0003, an operation unit 0004, a sending unit 0005, a receiving unit 0006, a sending/receiving control unit 0007, a beamformer unit 0008, a display unit 0009, a cross-section region information calculation unit 0011, a three-dimensional data storage unit 0012, an arbitrary cross-section image creation unit 0013, a three-dimensional coordinate transformation unit 0014, a volume data storage unit 0015, a three-dimensional image processing unit 0016, an image composition unit 0017, a projection processing unit 0018, a gradient calculation unit 0019, an arbitrary cross-section image storage unit 0020, and a cross-section image processing unit 0021, and the ultrasound diagnostic apparatus 0001 generates an image of an object in a three-dimensional space based on intensity volume data. Also, the ultrasound diagnostic apparatus 0001 is connected to an ultrasonic probe 0002.

The ultrasonic probe 0002 is used with being in contact with a diagnosing object 0010. The ultrasonic probe 0002 is formed of a plurality of transducers arranged therein, and has a function of sending/receiving an ultrasonic wave to/from the diagnosing object 0010 via the transducers. The ultrasonic probe 0002 is formed of the plurality of transducers having a rectangular shape or a fan-like shape, mechanically sweeps or manually moves the transducers in a direction perpendicular to an arrangement direction of the plurality of transducers, and thereby three-dimensionally sending/receiving of an ultrasonic wave is allowed. The ultrasonic probe 0002 may be an ultrasonic probe which has a plurality of transducers two-dimensionally arranged therein and can control sending/receiving of an ultrasonic wave electrically.

The control unit 0003 controls the respective components of the ultrasound diagnostic apparatus 0001 and the ultrasonic probe 0002. The operation unit 0004 conducts various inputs to the control unit 0003. The operation unit 0004 includes a keyboard, a trackball etc.

The sending unit 0005 makes the ultrasonic probe 0002 send an ultrasonic wave to the diagnosing object 0010 repeatedly at fixed time intervals. The sending unit 0005 drives the transducers of the ultrasonic probe 0002 to generate an emission pulse for generating an ultrasonic wave. The sending unit 0005 has a function of setting a convergence point of the sent ultrasonic waves at a certain depth. The receiving unit 0006 receives a reflection echo signal reflected from the diagnosing object 0010. The receiving unit 0006 amplifies a reflection echo signal received by the ultrasonic probe 0002 at a predetermined gain to generate an RF signal, i.e., a receipt signal. The sending/receiving control unit 0007 controls the sending unit 0005 and the receiving unit 0006.

The beamformer unit 0008 conducts phasing addition of the reflection echo received by the receiving unit 0006. The beamformer unit 0008 controls the phase of the RF signal amplified by the receiving unit 0006, forms an ultrasonic beam for one or plural convergence points, and generates RF signal frame data (corresponding to RAW data). The cross-section region information calculation unit 0011 forms a cross-section image based on the RF signal frame data generated by the beamformer unit 0008. The three-dimensional data storage unit 0012 stores a plurality of the cross-section images formed by the cross-section region information calculation unit 0011.

The arbitrary cross-section image creation unit 0013 creates a cross-section image based on the acquired shapes of the cross-section images. The three-dimensional coordinate transformation unit 0014 conducts three-dimensional coordinate transformation based on the acquired shapes of the cross-section images, generates intensity volume data, and stores the intensity volume data in the volume data storage unit 0015. The three-dimensional image processing unit 0016 creates illuminance volume data with use of the intensity volume data stored in the volume data storage unit 0015.

The gradient calculation unit 0019 creates gradient volume data with use of the intensity volume data stored in the volume data storage unit 0015. The projection processing unit 0018 conducts rendering processing with use of the illuminance volume data, the intensity volume data and the gradient volume data to generate a three-dimensional image. Also, the projection processing unit 0018 may create a three-dimensional image from the intensity volume data and the illuminance volume data. The image composition unit 0017 composes the three-dimensional image generated by the projection processing unit 0018 and the cross-section image created by the arbitrary cross-section image creation unit 0013. The display unit 0009 displays an image for display created by the image composition unit 0017.

Next, description will be given of processing of three-dimensional data. At the same time of sending/receiving of an ultrasonic wave, the ultrasonic probe 0002 switches a sending/receiving direction two-dimensionally, thereby the ultrasonic probe 0002 can conduct measurement, for example, along two axes, that is, θ and φ. Based on the set condition in the control unit 0003, the cross-section region information calculation unit 0011 receives the RF signal frame data output by the beamformer unit 0008, conducts signal processing such as gain correction, log compression, wave detection, contour emphasis, and smoothing processing, and forms two-dimensional cross-section region data.

The three-dimensional data storage unit 0012 has a function of storing a plurality of the two-dimensional cross-section region data, which is data output by the cross-section region information calculation unit 0011, based on the sending/receiving direction corresponding to an acquisition point. For example, a plurality of two-dimensional cross-section images created based on the measurement result of sending/receiving time series ultrasonic data, which has been subject to sampling in a depth direction, in the θ direction are obtained by driving in the φ direction perpendicular to the θ direction, and a plurality of two-dimensional cross-section region data associated with φ are stored as three-dimensional cross-section region data.

With use of the three-dimensional cross-section region data stored in the three-dimensional data storage unit 0012, the three-dimensional coordinate transformation unit 0014 conducts three-dimensional coordinate transformation to a coordinate in a space based on the acquisition point (depth, θ, φ), generates intensity volume data, and stores the generated intensity volume data in the volume data storage unit 0015.

With use of the three-dimensional cross-section region data stored in the three-dimensional data storage unit 0012, the arbitrary cross-section image creation unit 0013 creates an arbitrary cross-section image on an arbitrary plane in the three-dimensional space set by the control unit 0003 and the operation unit 0004, based on the acquisition point (depth, θ, φ).

The three-dimensional image processing unit 0016 creates illuminance volume data based on the intensity volume data stored in the volume data storage unit 0015. The gradient calculation unit 0019 creates volume data in which gradients in a visual line direction at respective voxel coordinates are calculated, based on the intensity volume data stored in the volume data storage unit 0015. The projection processing unit 0018 conducts rendering processing with use of the illuminance volume data and the intensity volume data, and generates a three-dimensional image.

The arbitrary cross-section image storage unit 0020 stores a plurality of the cross-section images created by the arbitrary cross-section image creation unit 0013. In the present embodiment, the arbitrary cross-section image storage unit 0020 stores cross-section region data of an arbitrary cross section region (cross section region to be observed by an operator) and cross-section images which are parallel to the cross-section region at equal intervals.

Figure 2:
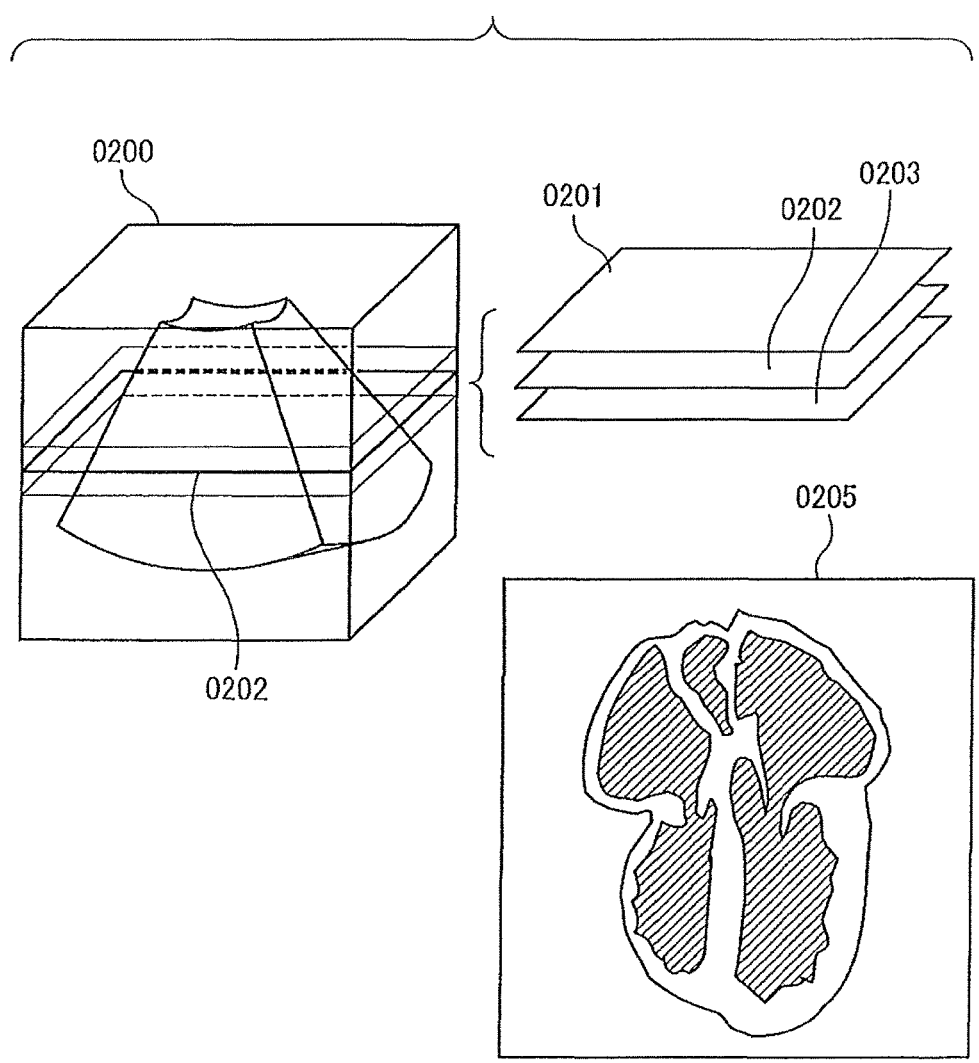
FIG. 2 is a schematic diagram illustrating a plurality of cross-section images stored in an arbitrary cross-section image storage unit.

FIG. 2 is a schematic diagram illustrating the plurality of cross-section images stored in the arbitrary cross-section image storage unit 0020. As illustrated in FIG. 2, the arbitrary cross-section image creation unit 0013 specifies cross-section region data 0202 of an arbitrary cross section in a three-dimensional space 0200 and creates a cross-section image 0205 from the cross-section region data 0202. The arbitrary cross-section image creation unit 0013 creates cross-section region data 0201 and 0203 having a thickness in a normal line direction of the cross-section region data 0202 which is set by the operator (or an interval parallel to the cross-section region data 0202, and set by the operator). The arbitrary cross-section image storage unit 0020 stores a plurality of the cross-section region data 0201, 0202, 0203. The cross-section image 0205 may be a cross-section image obtained by adding the cross-section region data 0201, 0202, 0203 and having a smoothing effect.

Next, detailed description will be given of the cross-section image processing unit 0021. The cross-section image processing unit 0021 creates a cross-section image with an emphasized shading effect, based on a plurality of the cross-section region data of cross-section images stored in the arbitrary cross-section image storage unit 0020.

Figure 3:
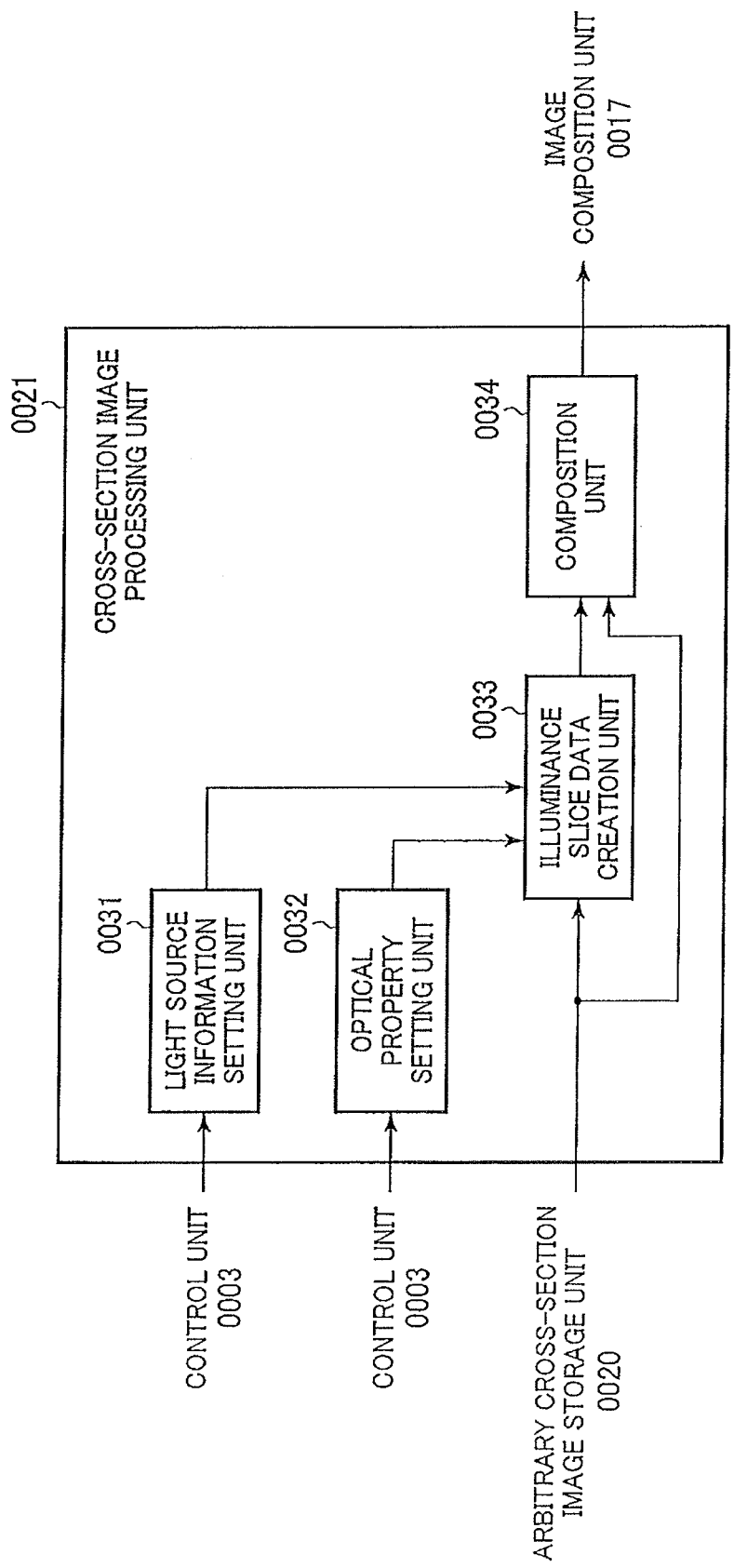
FIG. 3 is a block diagram illustrating an example of a cross-section image processing unit.

FIG. 3 is a block diagram illustrating an example of the cross-section image processing unit 0021. As illustrated in FIG. 3, the cross-section image processing unit 0021 includes a light source information setting unit 0031, an optical property setting unit 0032, an illuminance slice data creation unit 0033 and a composition unit 0034. The ultrasound diagnostic apparatus 0001 of the present embodiment includes the light source information setting unit 0031 which sets light source data indicating a property of a light source to be irradiated to a cross section region of an object, the optical property setting unit 0032 which sets a weight coefficient indicating an optical property of cross-section region data including intensity information on the cross section region to the light source, the illuminance slice data creation unit 0033 which calculates illuminance at a position corresponding to coordinates of a plurality of the cross section regions based on the light source data and the weight coefficient, and creates illuminance slice data of the plurality of the cross section regions based on the calculated illuminance, and the composition unit 0034 which composites a two-dimensional cross-section image of the object from the plurality of illuminance slice data. Furthermore, an ultrasound two-dimensional cross-section image generation-method of the present embodiment includes setting light source data indicating a property of a light source to be irradiated to a cross section region of an object, setting a weight coefficient indicating an optical property of cross-section region data including intensity information on the cross section region to the light source, calculating illuminance at positions corresponding to coordinates of a plurality of the cross section regions based on the light source data and the weight coefficient, creating illuminance slice data of the plurality of the cross section regions based on the calculated illuminance, and compositing a two-dimensional cross-section image of the object from the plurality of illuminance slice data.

The light source information setting unit 0031 sets light source data indicating a property of a light source to be irradiated to a cross section region of an object in a three-dimensional space. The light source information setting unit 0031 generates the light source data indicating intensity of the light source. Also, the light source information setting unit 0031 can set the light source data even by adjusting at least one of the intensity of the light source, a position of the light source in a three-dimensional space, a direction of the light source, a color tone of the light source, and a shape of the light source. For example, the light source information setting unit 0031 generates the light source data based on a direction of the light source, intensity of the light source, and a color tone of the light source which are input and set by the operation unit 0004 via the control unit 0003.

The optical property setting unit 0032 sets optical properties of the plurality of cross-section region data 0201, 0202, 0203 stored in the arbitrary cross-section image storage unit 0020. The optical property setting unit 0032 sets a weight coefficient indicating the optical property of the cross-section region data (cross-section region data including intensity information on the cross section region) to the light source. Based on the light source data set by the light source information setting unit 0031 and the optical property (weight coefficient) set by the optical property setting unit 0032, the illuminance slice data creation unit 0033 calculates illuminance arranged on the plurality of cross-section region data, and creates illuminance slice data. When the illuminance slice data creation unit 0033 creates the illuminance slice data of a plurality of cross section regions, the illuminance slice data creation unit 0033 calculates illuminance at a position corresponding to coordinates of the plurality of cross section regions based on the light source data and the weight coefficient.

The composition unit 0034 composites the two-dimensional cross-section image from the cross-section region data and the plurality of illuminance slice data. The composition unit 0304 composites the two-dimensional cross-section image of an object from the plurality of illuminance slice data. The composition unit 0034 may composite the two-dimensional cross-section image by using at least one of averaging illuminance values of the plurality of illuminance slice data, weighted addition of the plurality of slice data, and rendering processing by an opacity table referred to by the intensity information of the cross-section region data. Specifically, the composition unit 0034 may composite one cross-section image by averaging the illuminance values at positions respectively corresponding to the plurality of illuminance slice data (same coordinates on the cross section region). Also, the composition unit 0304 may composite one cross-section image by weighting each of the plurality of illuminance slice data and adding them (weighted addition of the illuminance values). Also, the composition unit 0034 is capable of compositing one cross-section image by weighting and adding the illuminance slice data and the intensity of the cross-section region data corresponding to the illuminance slice data. Specifically, the composition unit 0034 can composite a two-dimensional cross-section image from the cross-section region data and the plurality of illuminance slice data.

Next, description will be given of the light source data set by the light source information setting unit 0031, the optical property set by the optical property setting unit 0032 and the illuminance slice data created by the illuminance slice data creation unit 0033, using FIG. 4 and FIG. 5.

Figure 4:
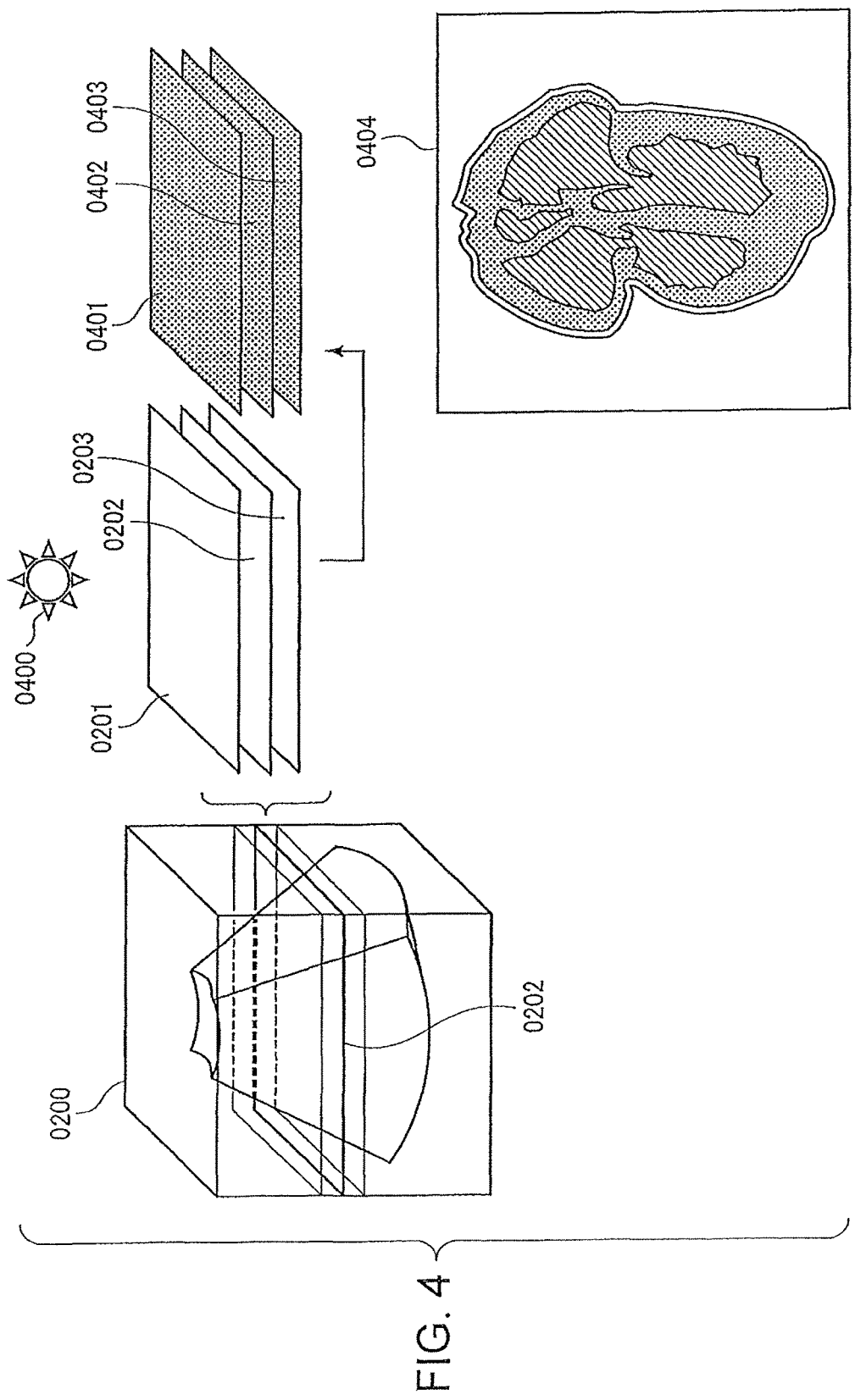
FIG. 4 is a schematic diagram schematically illustrating cross-section region data of an arbitrary cross section region, illuminance slice data and a light source.

FIG. 4 is a schematic diagram schematically illustrating cross-section region data of an arbitrary cross section region, illuminance slice data and a light source. As illustrated in FIG. 4, as in FIG. 2, the cross-section region data 0202 of an arbitrary cross section region is specified in the three-dimensional space 0200, and the cross-section region data 0201 and 0203, which are parallel to the cross-section region data 0202 of the cross section region in question. The arbitrary cross-section image storage unit 0020 stores the plurality of cross-section region data 0201, 0202, 0203.

Illuminance slice data 0401, 0402, 0403 correspond to the cross-section region data 0201, 0202, 0203, respectively. By calculating intensity of light of a light source 0400 which is set by the light source information setting unit 0031 when the light arrives at the cross-section region data 0201, 0202, 0203, the illuminance slice data 0401, 0402, 0403 are created.

The light source information setting unit 0031 generates light source data of the light source 0400 (intensity of light source). Light of the light source 0400 is propagated in a tissue shown by the cross-section region data 0201, 0202, 0203, and is leaked, absorbed, scattered, or reflected in the tissue. The illuminance slice data 0401, 0402, 0403, which reflect the behaviors of the light in the tissue (leakage, absorption, scattering, reflection, etc.), are created by the illuminance slice data creation unit 0033.

The optical property setting unit 0032 sets optical properties of the cross-section region data 0201, 0202, 0203, which are used to calculate the illuminance slice data 0401, 0402, 0403. The optical property setting unit 0032 sets weight coefficients indicating the optical properties of the cross-section region data 0201, 0202, 0203 to the light source. The illuminance slice data creation unit 0033 starts illuminance calculation from the cross-section region data 0201, which is disposed at the nearest position to the light source 0400, to the cross-section region data 0203, which is disposed at the furthest position. Specifically, in FIG. 4, the cross section region of the cross-section region data 0201 is an illuminance calculation starting slice, and the cross-section region of the cross-section region data 0203 is an illuminance calculation ending slice.

The illuminance slice data 0401, 0402, 0403 are created from the nearest to furthest positions to the light source 0400 in order, and the composition unit 0034 composites the illuminance slice data 0401, 0402, 0403, whereby a cross-section image 0404 is created.

Next, description will be given of an example of the configuration of the illuminance slice data creation unit 0033, using FIG. 5. As illustrated in FIG. 5, the illuminance slice data creation unit 0033 includes an illuminance slice data storage unit 0501, a light source data holding unit 0502, a two-dimensional convolution processing unit 0503, and a weighted addition unit 0504. The illuminance slice data creation unit 0033 includes the two-dimensional convolution processing unit 0503 which conducts two-dimensional convolution of the light source data, whereby generating two-dimensional convolution data, and the weighted addition unit 0504 which conducts weighted addition to the light source data and the two-dimensional convolution data based on the weight coefficient, whereby creating the illuminance slice data. Also, the illuminance slice data creation unit 0033 includes the light source data holding unit 0502 which holds, as light source slice data, an initial value of the light source data and a result of the weighted addition by the weighted addition unit 0504, and the illuminance slice data creation unit 0033, while switching the cross-section region data from the illuminance calculation starting slice to the illuminance calculation ending slice in the cross-section region data, conducts two-dimensional convolution of the light source slice data, whereby generating two-dimensional convolution data, and conducts weighted addition to the light source slice data and the two-dimensional convolution data based on the weight coefficient, whereby creating the illuminance slice data.

The light source data holding unit 0502 holds the light source slice data. The light source slice data has an initial value of the light source data set by the light source information setting unit 0031. The initial value of the light source data is set by the light source data holding unit 0502 before the illuminance slice data creation unit 0033 starts illuminance calculation.

The two-dimensional convolution processing unit 0503 conducts two-dimensional convolution of the light source slice data (light source data) held by the light source data holding unit 0502, whereby generating two-dimensional convolution data. The two-dimensional convolution is two-dimensional convolution processing of the light source slice data (light source data) and a convolution kernel indicating a scattering property, and the convolution kernel is configured by a two-dimensional matrix and set by the control unit. The weighted addition unit 0504 receives two-dimensional convolution slice data which is an output result of the two-dimensional convolution processing unit 0503 and the light slice data held by the light source data holding unit 0502. The weighted addition unit 0504 conducts weighted addition to the light source slice data (light source data) and the two-dimensional convolution slice data based on the weight coefficient, whereby generating the illuminance slice data. The weight coefficient is set by the optical property setting unit 0032.

The result of the weighted addition unit 0504 is stored in the illuminance slice data storage unit 0501 as illuminance slice data. Furthermore, the illuminance slice data, which is the result of the weighted addition unit 0504, is stored (held) in the light source data holding unit 0502 as light source slice data. Specifically, the light source data holding unit 0502 holds, as the light source slice data, the initial value of the light source data and the result of weighted addition by the weighted addition unit 0504. The two-dimensional convolution processing unit 0503 further conducts two-dimensional convolution of the light source slice data held by the light source data holding unit 0502.

Figure 6:
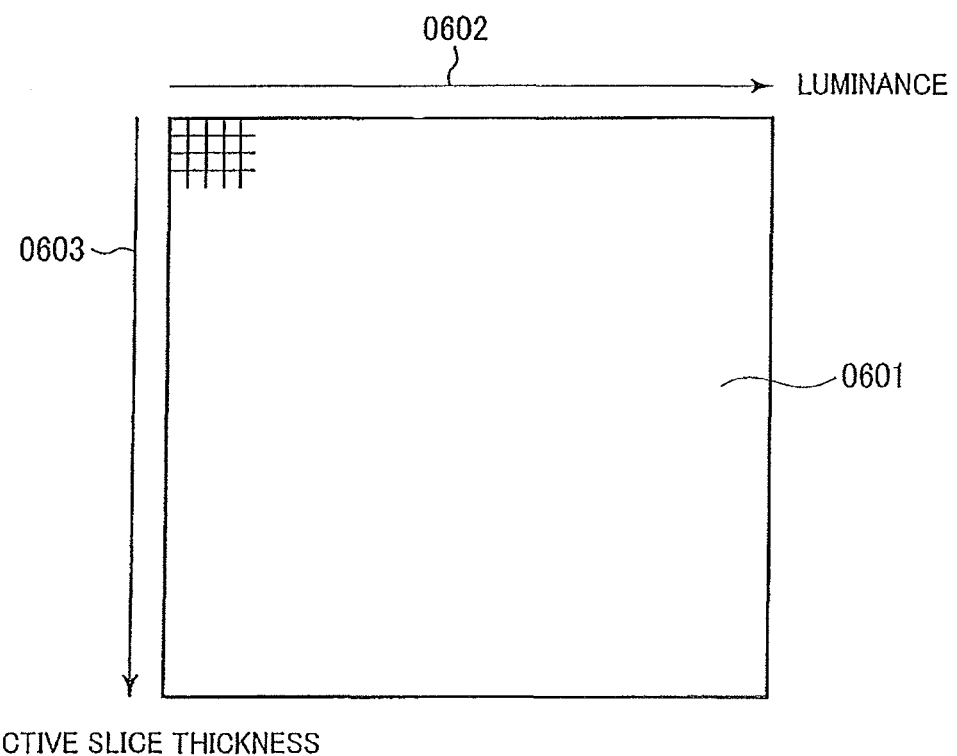
FIG. 6 is a diagram explaining setting of a weight coefficient used in a weighted addition unit.

Next, detailed description will be given of setting of a weight coefficient used by the weighted addition unit 0504, using FIG. 6. A two-dimensional weight coefficient table 0601 in FIG. 6, in which the weight coefficients set by the optical property setting unit 0032 are two-dimensionally arranged, is a two-dimensional table for referring to two-dimensionally arranged weight coefficients, using two indexes which are intensity of the cross-section region data of a cross section to be referred to and an effective slice thickness. The effective slice thickness means the number of slices of the cross-section region data in which effective intensity continue in a prescribed direction (for example, a visual line direction). The effective intensity value means a value of intensity which exceeds a preset threshold.

The optical property in the present embodiment is defined by a weight coefficient which is set so as to reproduce the behavior (action) of light, and is set by the optical property setting unit 0032, based on the optical property of the tissue. The optical property setting unit 0032 sets the two-dimensional weight coefficient table 0601 including weight coefficients, as the optical property of intensity volume data. Specifically, the optical property setting unit 0032 sets the weight coefficients, depending on the intensity of the cross-section region data and the number of the slices of the cross-section region data in which effective intensity continue in a prescribed direction (effective slice thickness).

Description will be given of a case where weight coefficients referred to in the two-dimensional weight coefficient table 0601 based on the two indexes which are intensity of the cross-section region data and the effective slice thickness are two, i.e., a and b. If a weight coefficient added to the light source slice data is a and a weight coefficient added to the two-dimensional convolution slice data is b, adjustment of magnitude of a and b allows easy setting of the behavior of light (degree of scattering, etc.).

Also, the weight coefficients a and b and an added sum of the light source data and the two-dimensional convolution slice data are output to the illuminance slice data storage unit 0501. When a total value of the weight coefficients a and b is set to be large, enhanced illuminance can be set, and when the total value of the weight coefficients a and b is set to be small, attenuated illuminance can be set.

The effective slice thickness means the number of slices in which effective intensity values in the same coordinate of the cross-section region data continue. The effective intensity value is determined based on whether intensity to be referred to exceeds a threshold. The threshold is set by the operation unit 0004 via the control unit 0003.

In the case of referring to the cross-section region data 0201, 0202, 0203 in FIG. 4 in order, if a intensity value of a coordinate to be referred to is larger than a threshold, the effective slice thickness increases, and if the intensity value is lower than the threshold, the effective slice thickness is initialized. On illuminance calculation of the illuminance slice data 0401, 0402, 0403, the weighted addition unit 0504 refers to a weight coefficient in the two-dimensional weight coefficient table 0601 based on the intensity value of the coordinate in question and the effective slice thickness. The weighted addition unit 0504 conducts weighted addition of the light source slice data and the two-dimensional convolution slice data, based on the weight coefficient.

According to the present embodiment, it is possible to set an optical property which is discriminated based on intensity corresponding to acoustic impedance of a living body and an effective slice thickness corresponding to a shape of the living body. Specifically, without complicated calculation, a two-dimensional weight coefficient table reflecting properties of a tissue is set, a behavior of light (degree of scattering, etc.) is adjusted based on the two-dimensional weight coefficient table, and thereby it is possible to give an optical effect in the tissue easily and arbitrarily, and the cross-section image 0404 in which reality is improved depending on a property of the tissue (for example, acoustic impedance of the tissue or corresponding hardness) can be created.

While switching the cross-section region data referred to by the weighted addition unit 0504 from the illuminance calculation starting slice (cross-section region data 0201) to the illuminance calculation ending slice (cross-section region data 0203), the illuminance slice data creation unit 0033 repeats the aforementioned illuminance calculation processing. Specifically, while switching the cross-section region data from the illuminance calculation starting slice to the illuminance calculation ending slice in the cross-section region data, the illuminance slice data creation unit 0033 conducts two-dimensional convolution of the light source slice data, whereby generating the two-dimensional convolution data, and conducts weighted addition of the light source slice data and the two-dimensional convolution data based on the weight coefficient, whereby creating the illuminance slice data.

After calculation to the illuminance calculation ending point is finished, the illuminance slice data creation unit 0033 creates the illuminance slice data in which illuminance to be arranged on the cross-section region data is calculated, and the illuminance slice data is stored in the illuminance slice data storage unit 0501.

A behavior property of light varies depending on wavelengths of a light source based on the law of nature. Accordingly, if reality is to be improved based on the law of nature, illuminance calculation is conducted for each wavelength of the light source. In this case, a weight coefficient varies for each wavelength of the light source.

The light source information setting unit 0031 sets light source data corresponding to a plurality of wavelengths of the light source. The optical property setting unit 0032 sets a weight coefficient for each of the plurality of wavelengths. Specifically, a plurality of the two-dimensional weight coefficient tables 0601 are prepared each for the wavelength, and the illuminance slice data creation unit 0033 conducts illuminance calculation processing for each wavelength to generate a plurality of illuminance slice data each for the wavelength. For example, if the light source 0400 has seven colors of visible rays, the illuminance slice data creation unit 0033 sets seven types of weight coefficient (or two-dimensional weight coefficient table) and generates seven types of illuminance slice data. Furthermore, if the light source 0400 has three primary colors of additive color mixture, the illuminance slice data creation unit 0033 sets three types of weight coefficient (or two-dimensional weight coefficient table) corresponding to wavelengths of elements R, G, B, and generates three types of illuminance slice data.

In the present embodiment, description will be given of a case where the light source 0400 has three primary colors of additive color mixture, three types of weight coefficient (or two-dimensional weight coefficient table) are set, and three types of illuminance slice data are generated.

Since three types of illuminance slice data for each wavelength (for each elements R, G, B) are generated, the composition unit 0034 composites the illuminance slice data for each wavelength to create three types (elements R, G, B) of a cross-section image for each wavelength. The illuminance slice data in the illuminance slice data storage unit 0501 are composited to the three types of the cross-section image for each wavelength by the composition unit 0034. By calculating an average of the illuminance values at the coordinates of the plurality of illuminance slice data for each wavelength, the composition unit 0034 can composite the three types of the cross-section image. Also, by weighting the plurality of illuminance slice data for each wavelength and adding them, the composition unit 0034 can composite the three types of the cross-section image. Also, by weighting and adding the illuminance slice data in the illuminance slice data storage unit 0501 and intensity of the cross-section region data corresponding to the illuminance slice data, the composition unit 0034 can composite one cross-section image.

When three types of the illuminance slice data for each wavelength are prepared, the composition unit 0034 (the cross-section image processing unit 0021) refers to the illuminance slice data for each wavelength, whereby generating three types of the cross-section image for each wavelength.

Also, the composition unit 0034 can create a cross-section image by using Equations (1) to (3) based on the three types of illuminance slice data for each wavelength and intensity of the cross-section region data corresponding to the illuminance slice data. As shown in Equations (1) to (3), the composition unit 0034 also can conduct rendering processing for creating a cross-section image, based on an illuminance value (voxel value) in the illuminance slice data L_r[k], L_g[k], L_b[k] for each wavelength (elements R, G, B), intensity (voxel value) C of the cross-section region data, and an opacity table α to be referred to by the intensity C. Specifically, the voxel values in the illuminance slice data L_r[k], L_g[k], L_b[k] for each wavelength are multiplied by opacity terms, which are obtained by the opacity table α to be referred to by the intensity C of the cross-section region data, and are accumulated in the visual line direction, and thereby the cross-section image is generated.

$$\text{OUT\_R}[K] = \Sigma^{k=0:K}((L\_r[k]) \cdot \alpha[C[k]] \cdot \Pi^{m=0:k-1}(1-\alpha[C[m]])) \quad (1)$$

$$\text{OUT\_G}[K] = \Sigma^{k=0:K}((L\_g[k]) \cdot \alpha[C[k]] \cdot \Pi^{m=0:k-1}(1-\alpha[C[m]])) \quad (2)$$

$$\text{OUT\_B}[K] = \Sigma^{k=0:K}((L\_b[k]) \cdot \alpha[C[k]] \cdot \Pi^{m=0:k-1}(1-\alpha[C[m]])) \quad (3)$$

In the equations, "k" indicates a slice number coordinate in a visual line direction. The visual line direction is set as a direction for observing an ultrasound image by the operation unit 0004 via the control unit 0003. The visual line direction determines an order for reference to the illuminance slice data and the cross-section region data. The illuminance slice data creation unit 0033 changes the order from the illuminance calculation starting slice to the illuminance calculation ending slice, based on the visual line direction. As illustrated in FIG. 4, based on the visual line direction, it is possible to conduct composition calculation in order from the illuminance slice data 0401 to 0403, and it is also possible to conduct composition calculation in order from the illuminance slice data 0403 to 0401. In this case, the cross-section region data corresponding the illuminance slice data are also referred to in the same order as the illuminance slice data based on the visual line direction, in the case of conducting composition calculation in order from the illuminance slice data 0401 to 0403, the cross-section region data are referred to in order from the cross-section region data 0201 to 0203, while in the case of conducting composition calculation in order from the illuminance slice data 0403 to 0401, the cross-section region data are referred to in order from the cross-section region data 0203 to 0201.

The cross-section image created by the cross-section image processing unit 0021 is arranged on the same screen as an arbitrary cross-section image or a three-dimensional image by the image composition unit 0017, and is displayed by the display unit 0009. In this case, the image composition unit 0017 converts as appropriate the cross-section image divided for each wavelength so as to correspond to an input standard of the display unit 0009.

Figure 7:
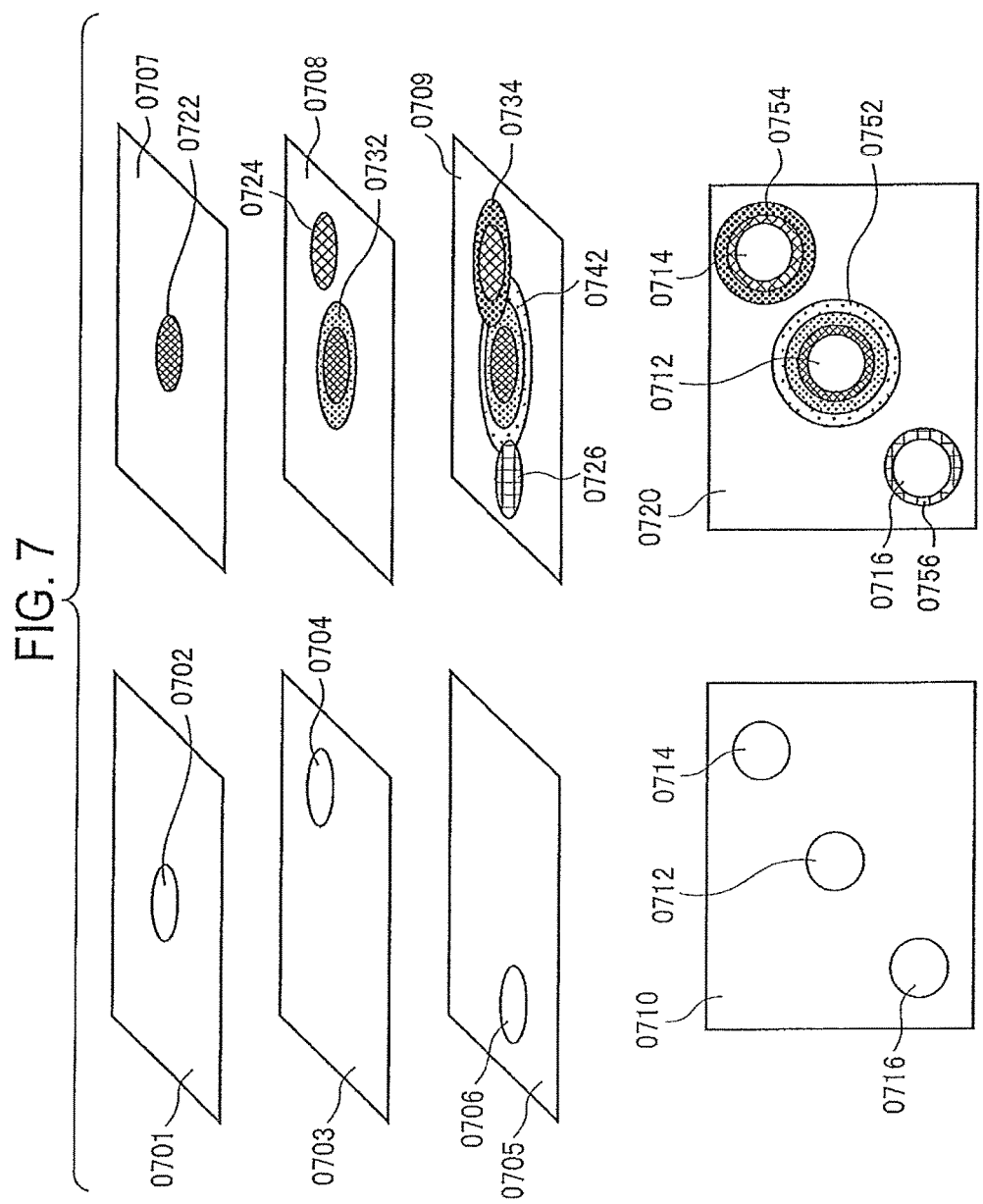
FIG. 7 is a diagram illustrating an example of effects of the present embodiment.

Description will be given of effects of the present embodiment, using FIG. 7. As illustrated in FIG. 7, structures with high intensity (e.g., tissue) 0702, 0704, 0706 appear on cross-section images of cross-section region data 0701, 0703, 0705. When the three cross-section region data are composited, the structures with high intensity 0702, 0704, 0706 are displayed simultaneously in the cross-section image, as illustrated in a composition image 0710. For example, the structure 0702 on the cross-section region data 0701 is displayed as a high-intensity portion 0712 on the composition image 0710. The structure 0704 on the cross-section region data 0703 is displayed as a high-intensity portion 0714 on the composition image 0710. The structure 0706 on the cross-section region data 0705 is displayed as a high-intensity portion 0716 on the composition image 0710.

Illuminance slice data 0707, 0708, 0709 illustrated in FIG. 7 correspond to the cross-section region data 0701, 0703, 0705, respectively. The illuminance slice data 0707, 0708, 0709 in FIG. 7 illustrate the case where illuminance calculation is conducted by the illuminance slice data creation unit 0033, in order from the illuminance slice data 0707 to 0709, based on the visual line direction.

The illuminance slice data 0707 is provided with an optical property referring to the intensity of the cross-section region data 0701, and an illuminance structure 0722 reflecting the optical property of the structure 0702 is generated. The illuminance slice data 0708 is provided with an optical property referring to the intensity of the cross-section region data 0703, and an illuminance structure 0724 reflecting the optical property of the structure 0704 is generated, and also, the illuminance structure 0722 generated in the illuminance slice data 0707 appears as an illuminance structure 0732 with an effect of two-dimensional convolution processing.

The illuminance slice data 0709 is provided with an optical property referring to the intensity of the cross-section region data 0705, and an illuminance structure 0726 reflecting the optical property of the structure 0706 is generated and also, the illuminance structures 0724, 0732 generated in the illuminance slice data 0708 appear as illuminance structures 0734, 0742 with an effect of two-dimensional convolution processing.

In this way, the illuminance slice data creation unit 0033 calculates illuminance arranged on the plurality of cross-section region data 0701, 0703, 0705 based on the light source data (a position of the light source, a direction of the light source, intensity and color of the light source, etc.) and the optical properties, and creates the illuminance slice data 0707, 0708, 0709. In the illuminance slice data 0709, the illuminance structure 0726 is generated based on the cross-section region data 0705, and also the illuminance structures 0722, 0724 generated in the illuminance slice data 0707, 0708 appear as the illuminance structures 0734, 0742 reflecting behaviors of light, with an effect of two-dimensional convolution processing.

While switching the cross-section region data referred to by the weighted addition unit 0504 from the illuminance calculation starting slice (cross-section region data 0701) to the illuminance calculation ending slice (cross-section region data 0705), the illuminance slice data creation unit 0033 repeats the aforementioned illuminance calculation processing. For example, illuminance calculation processing of the illuminance structure 0722 generated in the illuminance slice data 0707 is repeatedly conducted by the illuminance slice data creation unit 0033, and thereby the illuminance structure 0742 appears.

The composition unit 0034 composites the three illuminance slice data 0707, 0708, 0709 and the three cross-section region data 0701, 0703, 0705, and generates the cross-section image 0710. To the cross-section image 0710, effects of the high-intensity portions 0712, 0714, 0716 as well as the illuminance structures 0752, 0754, 0756 are reflected. For example, the structure 0702 on the cross-section region data 0701 is displayed as an image in which the structure is further emphasized, with the high-intensity portion 0712 and an optical effect (illuminance structure 0752) on the composited cross-section image 0710.

Figure 8:
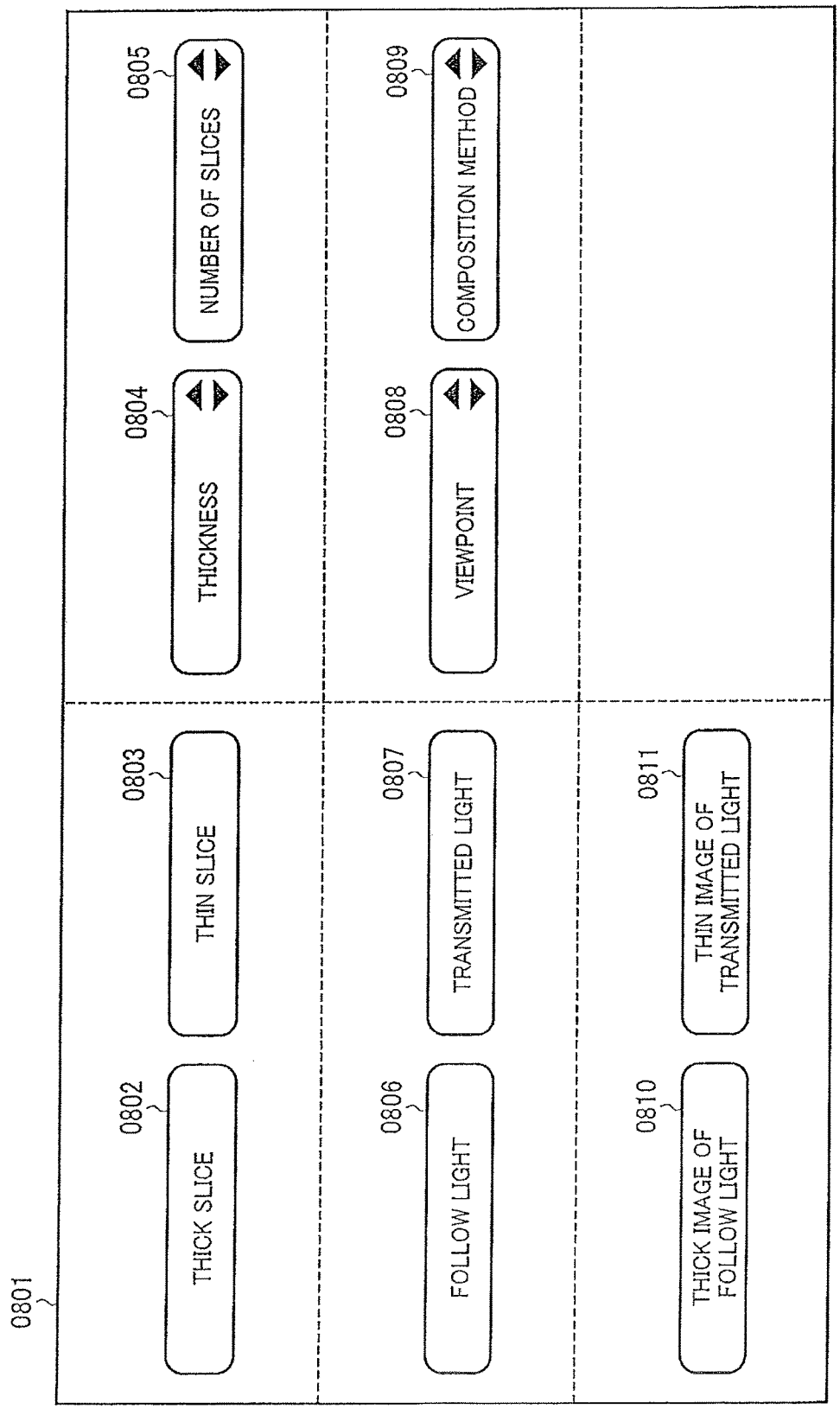
FIG. 8 is a diagram illustrating an example of a graphical user interface switching a display mode of a cross-section image.

FIG. 8 is a diagram illustrating an example of a graphical user interface switching a display mode of a cross-section image. As illustrated in FIG. 8, the display unit 0009 displays a switch button screen 0801 for switching the display modes of the illuminance slice data and the cross-section image. Switching the button on the switch button screen 0801 by the operation unit 0004 via the control unit 0003 allows the display modes of the illuminance slice data and the cross-section image to be switched.

A button 0802 and a button 0803 are an interface (first setting unit) for selecting a thickness in a visual line direction corresponding to a plurality of cross-section region data for creating a cross-section image. If the button 0802 is selected, the plurality of cross-section region data are set in a wide region in the visual line direction. If the plurality of cross-section region data are set in the wide region in the visual line direction, an optical effect can be provided to the cross-section image over the wide region, for example, a darker shading effect can be provided, and thereby the structure can be further emphasized. On the other hand, if the button 803 is selected, the plurality of cross-section region data are set in a narrow region in the visual line direction. If the plurality of cross-section region data are set in the narrow region in the visual line direction, an optical effect can be provided to the cross-section image in the narrow region, and thereby light is easy to be transmitted and the internal structure can be recognized transparently. That is, the button 0802 and the button 0803 set a width of the region in the visual line direction for setting the plurality of the cross section regions.

With use of a button 0804 (second setting unit), an arbitrary thickness in a normal line of the cross-section region data (for example, the cross-section region data 0202 in FIG. 2) may be set. Alternately, with use of a button 0805 (third setting unit), an arbitrary number of slices of the cross-section region data may be set. The button 0804 and the button 0805 also make it possible to adjust the intervals of the cross-section region data by setting an arbitrary thickness and an arbitrary number of slices at equal intervals.

Furthermore, with use of a button 0806 (fourth setting unit) and a button 0807 (fourth setting unit), even an illumination direction of light can be selected (set). If the illumination direction of light is set as follow light, the directions of the light source and the viewpoint are made to be coincident with each other, and thereby a cross-section image such as a macro specimen for a naked eye can be created. If the illumination direction of light is set as transmitted light, the direction of the light source and the direction of the viewpoint are reversed, and thereby a cross-section image such as a micro specimen to be exposed to light from the rear can be created. Moreover, with use of a button 0808 (fifth setting unit), the follow direction or the opposite direction of the viewpoint is changed, and thereby even a visual line direction can be changed.

Furthermore, with use of a button 0809 (sixth setting unit), even a composition method executed by the composition unit 0034 (for example, averaging illuminance values, weighted addition of illuminance values) can be selected (set). Also, even the two-dimensional weight coefficient table 0601 used by the weighted addition unit 0504 can be changed.

The ultrasound diagnostic apparatus 0001 of the present embodiment includes the display unit 0009 displaying a two-dimensional cross-section image, and the display unit 0009 displays at least one or a combination of two or more of the first setting unit setting the width of a region in a visual line direction for setting the plurality of the cross section regions, the second setting unit setting an arbitrary thickness in a normal direction of the cross-section region data, the third setting unit setting the number of slices of the cross-section region data, the fourth setting unit setting the illumination direction of the light source, the fifth setting unit changing the follow direction or the opposite direction of a viewpoint, and the sixth setting unit setting the composition method by the composition unit. Specifically, if a plurality of conditions are provided to a button, the plurality of conditions can also be changed at the same time.

A button 0810 and a button 0811 are a button provided with conditions of a thickness and an illumination direction of light. The button 0810 allows setting a thickness to be increased and setting light as follow light to be executed at the same time, and thus, it is possible to set a range in which a plurality of cross-section region data are created to be wide, make the directions of the light source and the viewpoint coincident with each other, and create a cross-section image such as a macro specimen for a naked eye. The button 0811 allows setting a thickness to be decreased and setting light as transmitted light to be executed at the same time, and thus, it is possible to set a range in which a plurality of cross-section region data are created to be narrow, reverse the direction of the light source and the direction of the viewpoint, and create a cross-section image such as a micro specimen to be exposed to light from the rear. Also, the two-dimensional weight coefficient table 0601 which indicates the optical property coincident with desired display may be changed simultaneously.

In this way, if setting of the display mode of the cross-section image is changed by the interface included in the display unit 0009 or the operation unit 0004, a drawn range or the number of slices of the cross-section image is set by the arbitrary cross-section image creation unit 0013, the illumination direction is set by the light source information setting unit 0031, and the two-dimensional weight coefficient table 0601 is set by the optical property setting unit 0032, via the control unit 0003.

Figure 9:
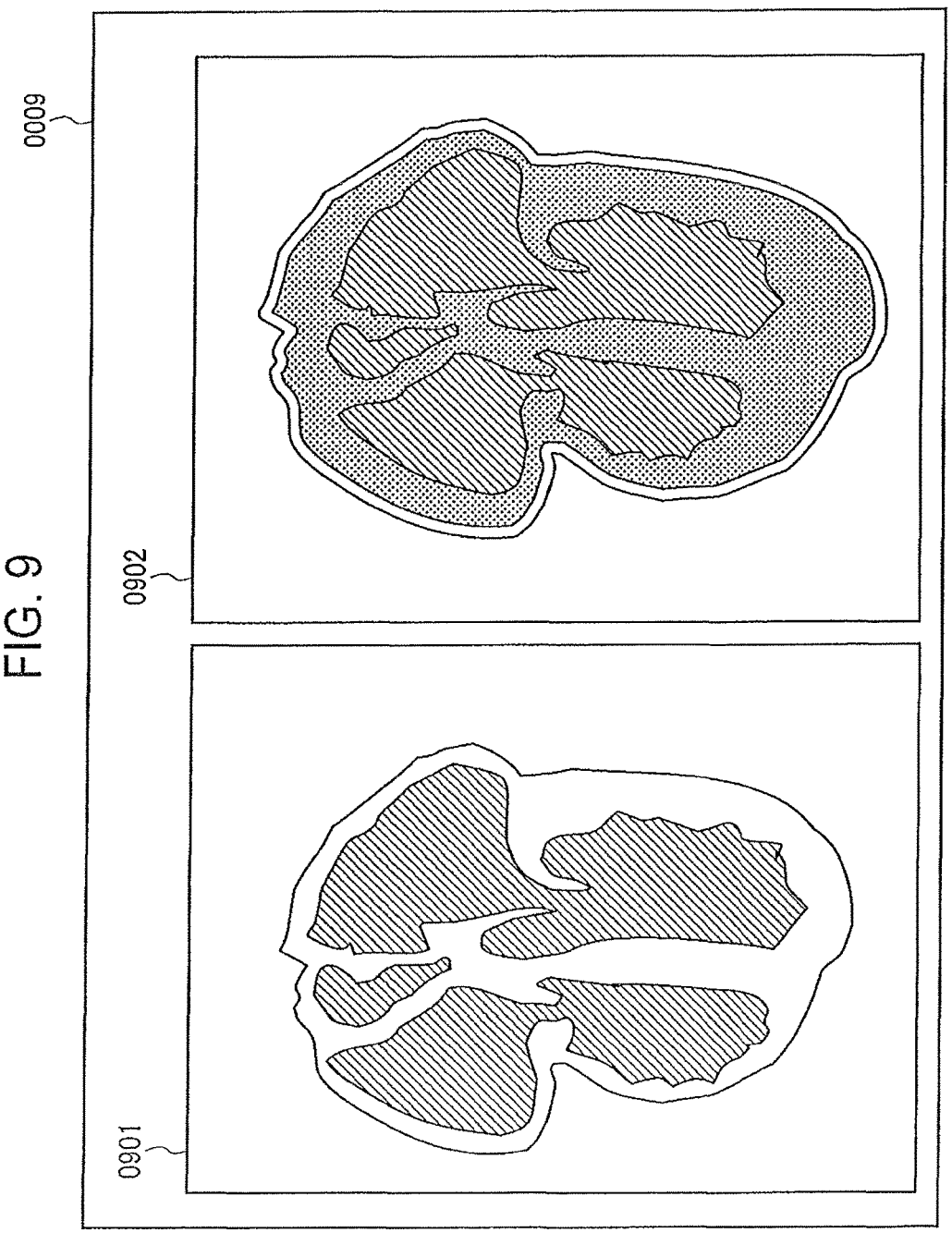
FIG. 9 is a diagram illustrating a mode in which an arbitrary cross-section image by an ultrasonic wave and a same cross section region in a cross-section image are displayed simultaneously.

Next, description will be given of a display mode in the present embodiment, using FIG. 9. FIG. 9 is a diagram illustrating a mode in which an arbitrary cross-section image by an ultrasonic wave and a same cross section region in a cross-section image are displayed simultaneously. As illustrated in FIG. 9, the display unit 0009 displays a cross-section image 0901 which is a conventional cross-section image and a cross-section image (two-dimensional cross-section image) 0902 of the present embodiment, simultaneously. Specifically, the display unit 0009 displays the cross-section image 0901 of the cross section region and the two-dimensional cross-section image 0902 corresponding to the cross-section image of the cross section region, in parallel. As a result, while conducting a diagnosis with the cross-section image 0901 based on the conventional diagnostic criteria, it is possible to improve the accuracy of the diagnosis with use of the cross-section image 0902 in which the structure of a tissue can be clearly seen.

Figure 10:
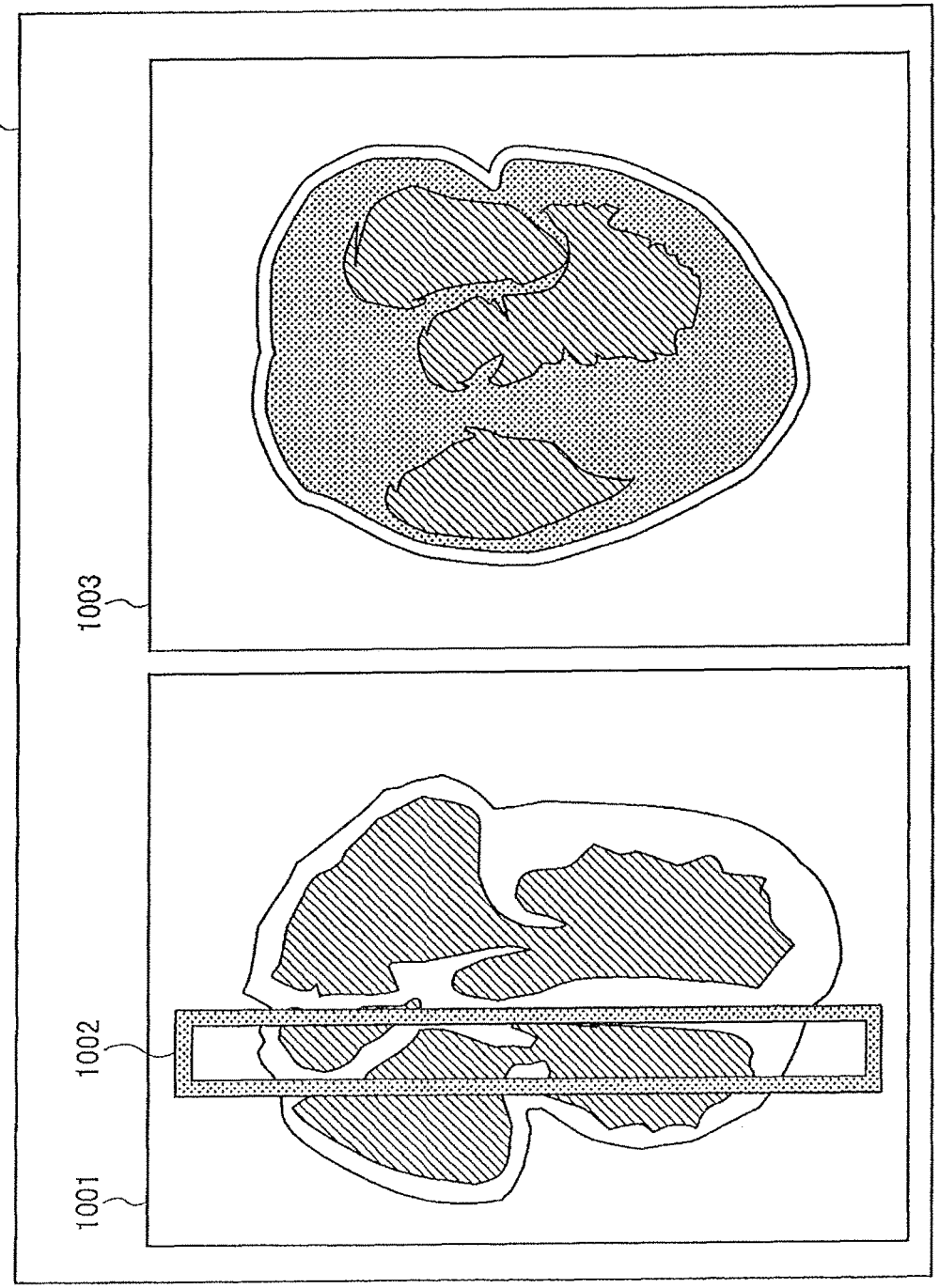
FIG. 10 is a diagram illustrating a mode in which an arbitrary cross-section image by an ultrasonic wave and a cross-section image perpendicular to the cross-section image in question are displayed simultaneously.

Next, description will be given of another display mode in the present embodiment, using FIG. 10. FIG. 10 is a diagram illustrating a mode in which an arbitrary cross-section image by an ultrasonic wave and a cross-section image perpendicular to the cross-section image in question are displayed simultaneously. As illustrated in FIG. 10, the display unit 0009 displays a conventional cross-section image 1001 and a cross-section image (two-dimensional cross-section image) 1003, which is a cross-section image according to the present embodiment, perpendicular to the cross-section image 1001, simultaneously. In the cross-section image 1001, a cross-section image setting frame 1002 is displayed. The cross-section image 1001 is used as a guide for setting the cross-section image setting frame 1002.

The cross-section image setting frame 1002 is a frame for determining a drawing range of the cross-section image 1003 perpendicular to the cross-section image 1001, a plurality of arbitrary cross-section images are formed within the range determined by the cross-section image setting frame 1002, and the cross-section image 1003 is created and displayed based on the plurality of the formed cross-section region data. Specifically, the cross-section image setting frame 1002 specifies positions of a plurality of cross section regions to create a plurality of illuminance slice data. The cross-section image 1003 is an image on a plane perpendicular to the cross-section image 1001, and the cross-section image 1003 as well as the cross-section image 1001 is set to be observable, and thus, inspection efficiency can be improved.

Figure 11:
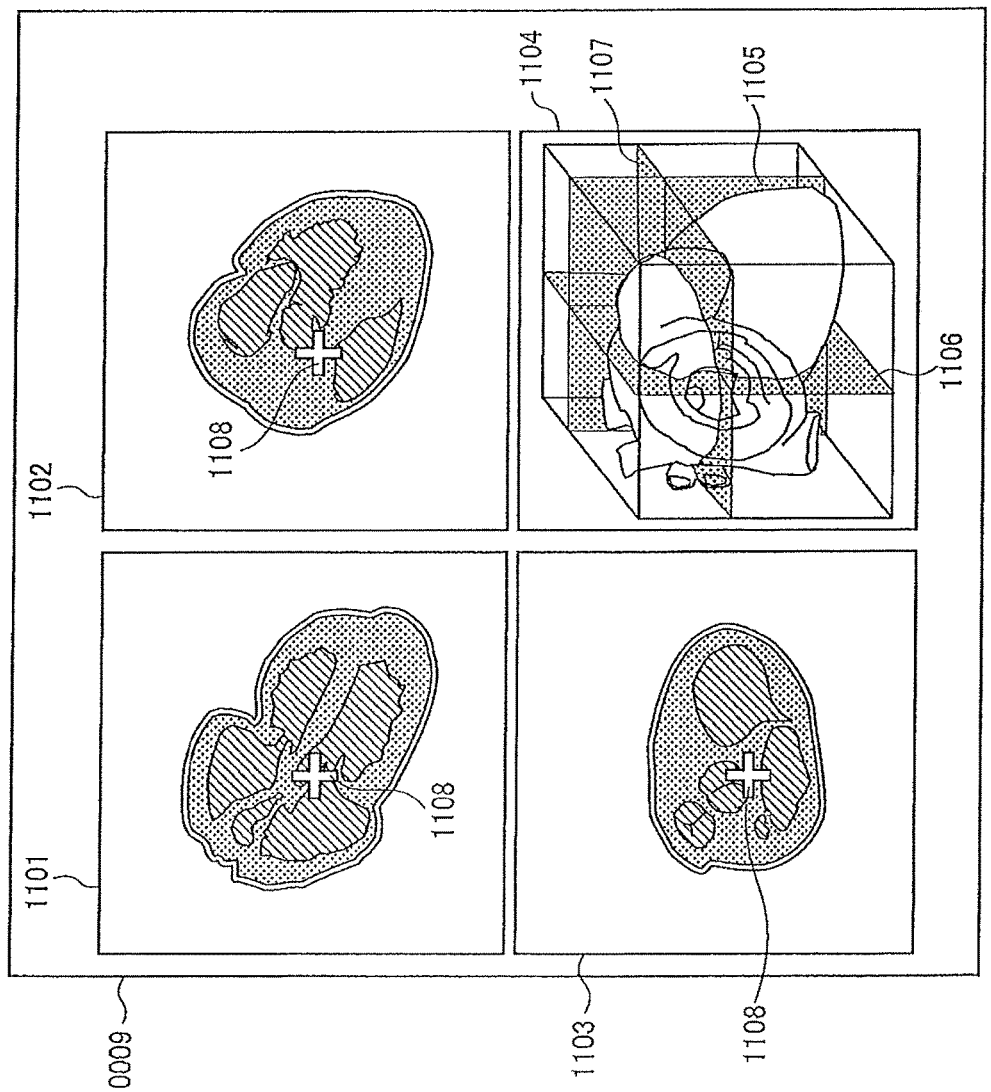
FIG. 11 is a diagram illustrating a mode in which two-dimensional cross-section images of three planes which are perpendicular to one another in a three-dimensional space and a three-dimensional image are displayed simultaneously.

Next, description will be given of yet another display mode in the present embodiment, using FIG. 11. FIG. 11 is a diagram illustrating a mode in which two-dimensional cross-section images of three planes which are perpendicular to one another in a three-dimensional space and a three-dimensional image are displayed simultaneously. As illustrated in FIG. 11, cross-section images (two-dimensional cross-section images) 1101, 1102, 1103 on three perpendicular planes having a common point of intersection and a three-dimensional image 1104 are displayed simultaneously by the display unit 0009.

In the three-dimensional image 1104, cross-section image setting marks 1105, 1106, 1107, which correspond to the cross-section images 1101, 1102, 1103, respectively, are displayed. If the cross-section image setting mark 1105, 1106 or 1107 moves, the corresponding cross-section image 1101, 1102 or 1103 moves. If one of the cross-section image setting marks 1105, 1106, 1107 is selected on the three-dimensional image of the display unit 0009, the cross-section image setting mark 1105, 1106 or 1107 can be moved with a trackball or a cursor. Also, by operation of an encoder, the cross-section image setting marks 1105, 1106, 1107 can be moved in an arbitrary direction directly.

Furthermore, in each cross-section images 1101, 1102, 1103, a point mark of intersection 1108 which is the common point of intersection is displayed, and moving the point mark of intersection 1108 allows the positions of the cross-section images 1101, 1102, 1103 to be moved. The position of the point mark of intersection 1108 corresponds to the position of the point of intersection of the cross-section image setting marks 1105, 1106, 1107 in the three-dimensional image 1104, and moving the point mark of intersection 1108 causes the cross-section image setting marks 1105, 1106, 1107 to move, as well. As a result, the positions of the cross-section images 1101, 1102, 1103 are also moved. The point mark of intersection 1108 may be moved with a trackball or a cursor by selecting the point mark of intersection 1108 on the display unit 0009, or the point mark of intersection 1108 may be moved in an arbitrary direction directly by operation of an encoder.

By using the display mode illustrated in FIG. 11, it is possible to observe the cross-section images 1101, 1102, 1103 and the three-dimensional image 1104 simultaneously, and thus, the inspection efficiency can be improved. Also, the display positions of the cross-section images 1101, 1102, 1103 can be easily operated, and thus, the inspection efficiency can be improved.

That is, in the case of displaying the two-dimensional cross-section image perpendicular to the cross-section image, the display unit 0009 displays the cross-section image setting frame 1002 specifying the positions of the plurality of cross section regions for creating the plurality of illuminance slice data, in the case of displaying the plurality of two-dimensional cross-section images perpendicular to one another in the three-dimensional space, the display unit 0009 displays the point mark of intersection 1108 which is the common point of intersection, and in the case of displaying the plurality of two-dimensional cross-section images perpendicular to the cross-section image and parallel to one another, the display unit 0009 displays cross-section image setting lines 1302 to 1309 specifying the positions of the cross section regions corresponding to the plurality of two-dimensional cross-section images.

Figure 12:
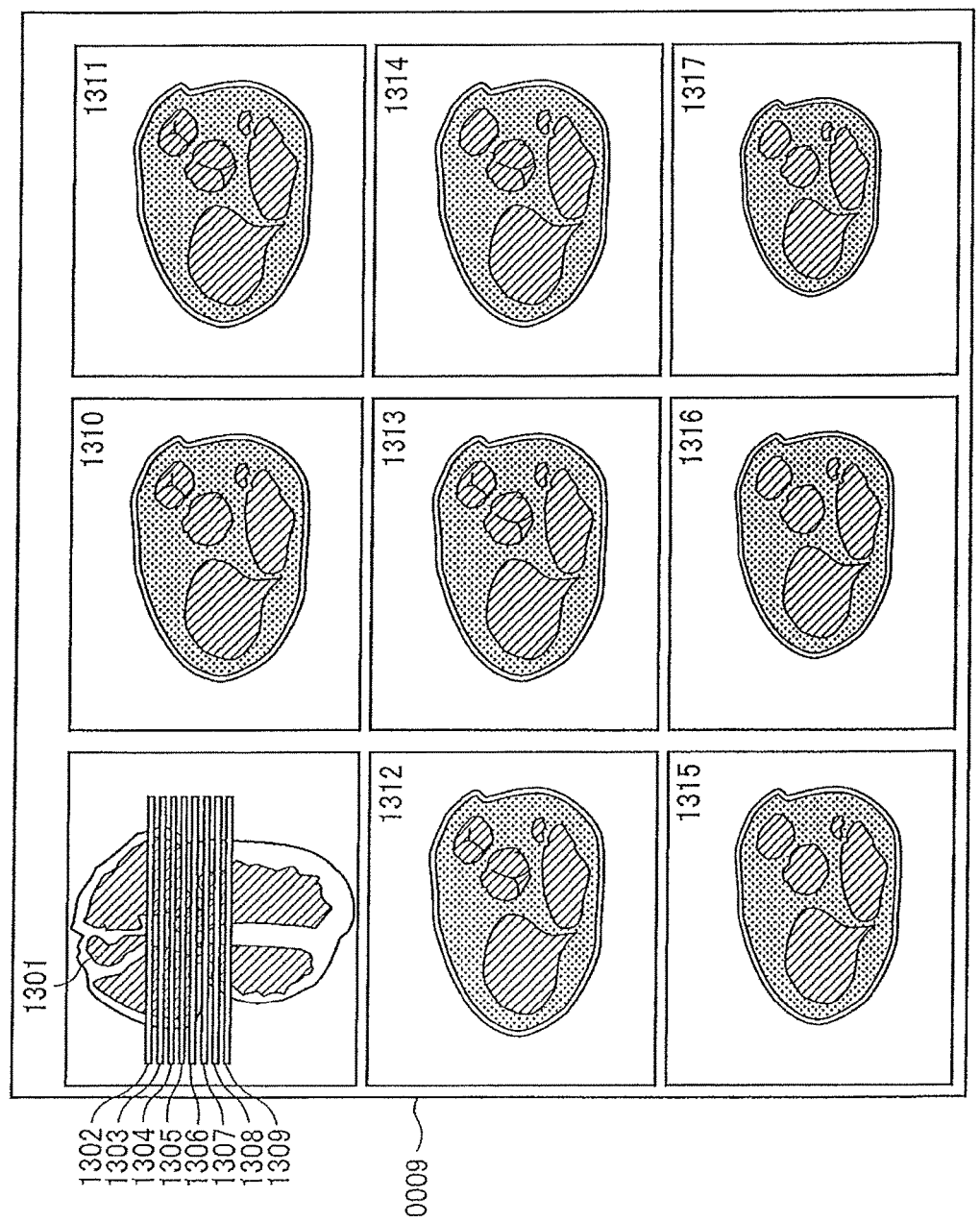
FIG. 12 is a diagram illustrating an example of a display mode in which one or more arbitrary cross-section images by an ultrasonic wave and a plurality of cross-section images perpendicular to one another are displayed simultaneously.

Next, description will be given of yet another display mode in the present embodiment, using FIG. 12. FIG. 12 is a diagram illustrating an example of a display mode in which one or more arbitrary cross-section images by an ultrasonic wave and a plurality of cross-section images perpendicular to one another are displayed simultaneously. As illustrated in FIG. 12, an arbitrary cross-section image 1301 is used as a guide. In the cross-section image 1301, the cross-section image setting lines 1302, 1303, 1304, 1305, 1306, 1307, 1308, 1309 are displayed. The cross-section image setting lines 1302 to 1309 are a line for determining drawing positions of cross-section images 1310 to 1317. The cross-section image setting lines 1302 to 1309 specify positions of cross section regions corresponding to the plurality of two-dimensional cross-section images. The cross-section images (two-dimensional cross-section images) 1310, 1311, 1312, 1313, 1314, 1315, 1316, 1317 corresponding to the positions determined by the cross-section image setting lines 1302 to 1309, respectively, are displayed on the display unit 0009. The cross-section images 1310 to 1317 are cross-section images which are perpendicular to the arbitrary cross-section image 1301 and parallel to one another, the plurality of cross-section images 1310 to 1317 are set at the same time with use of the cross-section image 1301 as a guide, and thus, the inspection efficiency can be improved.

Specifically, the display unit 0009 displays at least one of the two-dimensional cross-section image corresponding to the cross-section image of the cross section region, the two-dimensional cross-section image perpendicular to the cross-section image, the plurality of the two-dimensional cross-section images perpendicular to one another in the three-dimensional space, and the plurality of the two-dimensional cross-section images perpendicular to the cross-section image and parallel to one another.

The present embodiment has been described so far, but the present invention is not limited to the present embodiment, and modification and change within the range set forth in the claims are possible.

Figure 13:
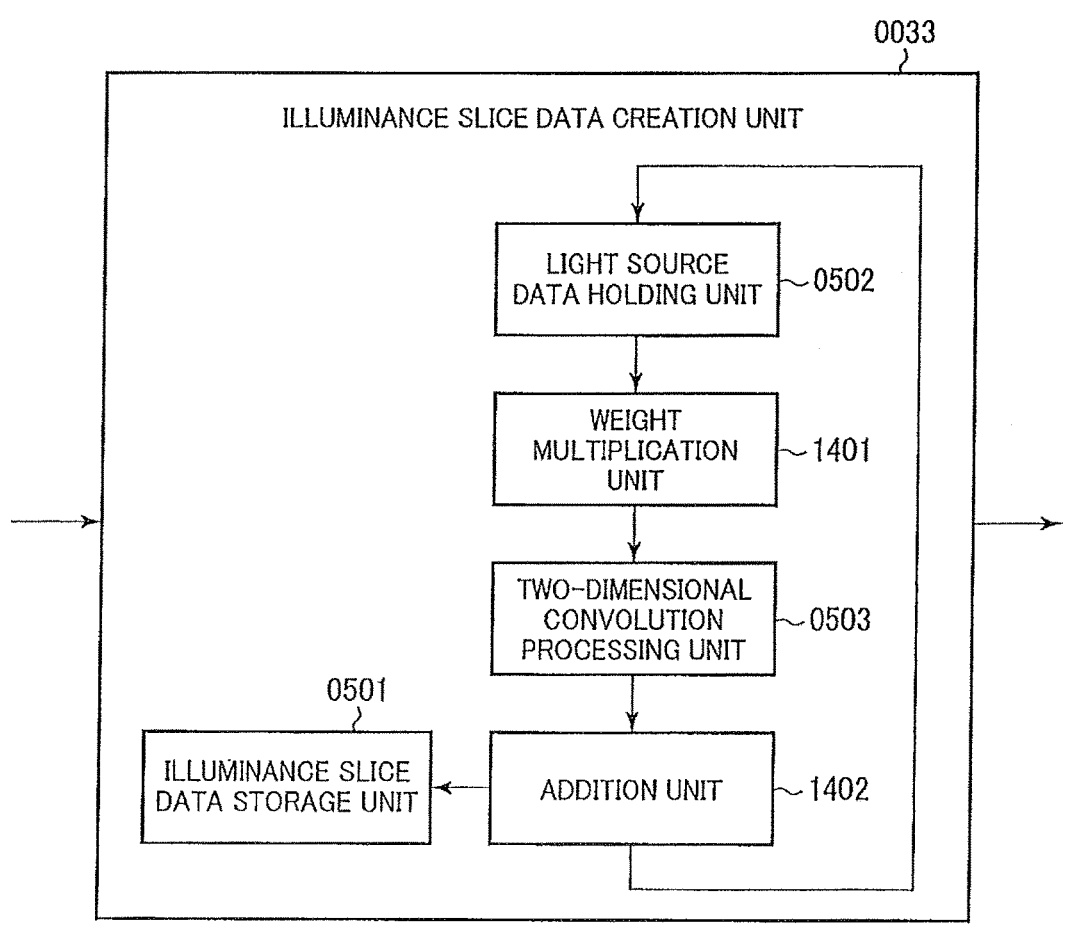
FIG. 13 is a block diagram illustrating an illuminance slice data creation unit according to a modification example of the present embodiment.

FIG. 13 is a block diagram illustrating a modification example of the present embodiment. As illustrated in FIG. 13, the illuminance slice data creation unit 0033 of the ultrasound diagnostic apparatus 0001 includes the light source data holding unit 0502, a weight multiplication unit 1401, the two-dimensional convolution processing unit 0503, and an addition unit 1402. The light source data holding unit 0502 and the two-dimensional convolution processing unit 0503 have the same functions as those in the present embodiment.

Figure 5:
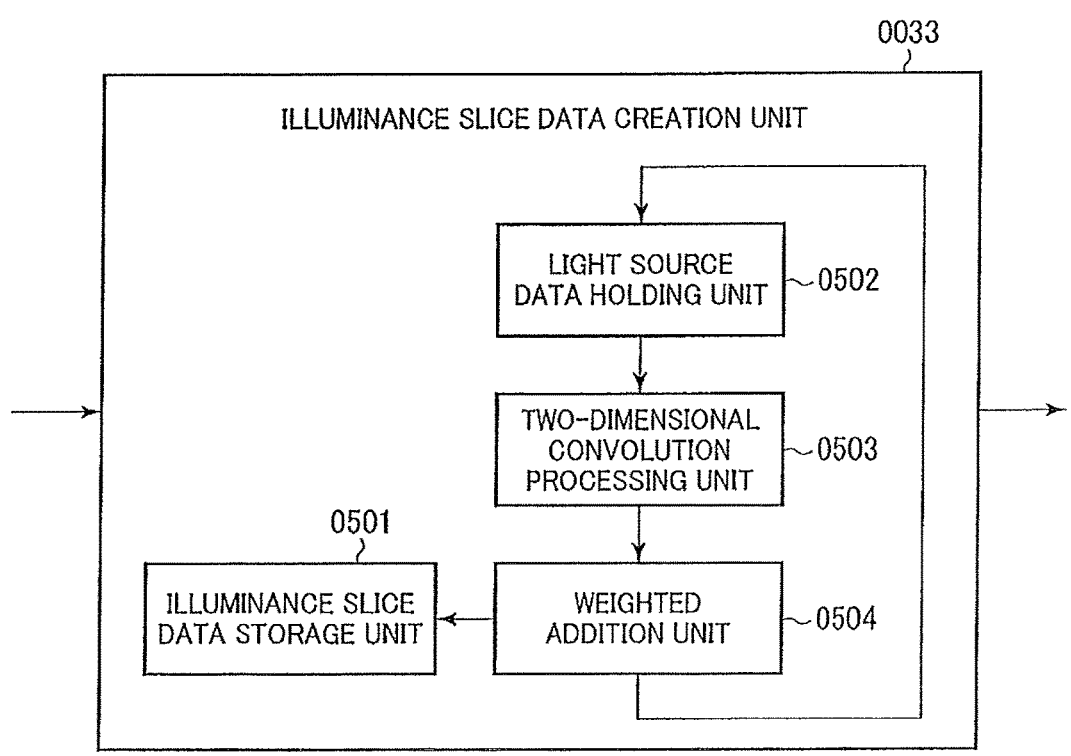
FIG. 5 is a block diagram illustrating an example of a configuration of an illumination slice data creation unit.

Comparing with the illuminance slice data creation unit 0033 in FIG. 5, the addition unit 1402 is provided in place of the weighted addition unit 0504, and the weight multiplication unit 1401 is provided in the front stage of the two-dimensional convolution processing unit 0503.

With use of the two-dimensional weight coefficient table 0601 set by the optical property setting unit 0032, the weight multiplication unit 1401 refers to the two-dimensional weight coefficient table 0601 based on intensity (axis 0602) of the cross-section image (cross-section region data) and the effective slice thickness (axis 0603), and obtains two weight coefficients (for example, a and b described above). The weight multiplication unit 1401 receives the light source slice data held by the light source data holding unit 0502 and outputs weighted light source slice data obtained by multiplying the weight coefficient a to the light source slice data and weighted light source slice data obtained by multiplying the weight coefficient b to the light source slice data. One of the two weighted light source slice data obtained by multiplying the weight coefficients a and b (for example, the weighted light source slice data obtained by multiplying the weight coefficient a) is input to the two-dimensional convolution processing unit 0503. The two-dimensional convolution processing unit 0503 conducts two-dimensional convolution of the input weighted light source slice data, and creates two-dimensional convolution slice data.

The other of the two weighted light source slice data obtained by multiplying the weight coefficients a and b by the weight multiplication unit 1401 (for example, the weighted light source slice data obtained by multiplying the weight coefficient b) is input, as light source slice data, to the addition unit 1402. The addition unit 1402 receives and adds the light source slice data and the two-dimensional convolution slice data, and stores the added data in the illuminance slice data storage unit 0501.

According to the modification example illustrated in FIG. 13, as in the present embodiment, by multiplying the weight coefficient to the light source slice data held by the light source data holding unit 0502 and the two-dimensional convolution slice data obtained by conducting two-dimensional convolution of the light source slice data and adding them, a behavior of light (degree of scattering, etc.) can be easily set by the weight coefficient which is set so as to reproduce the behavior (action) of light in the tissue, and it is possible to obtain a cross-section image in which reality is improved based on the illuminance slice data reflecting the behavior of light.

Figure 14:
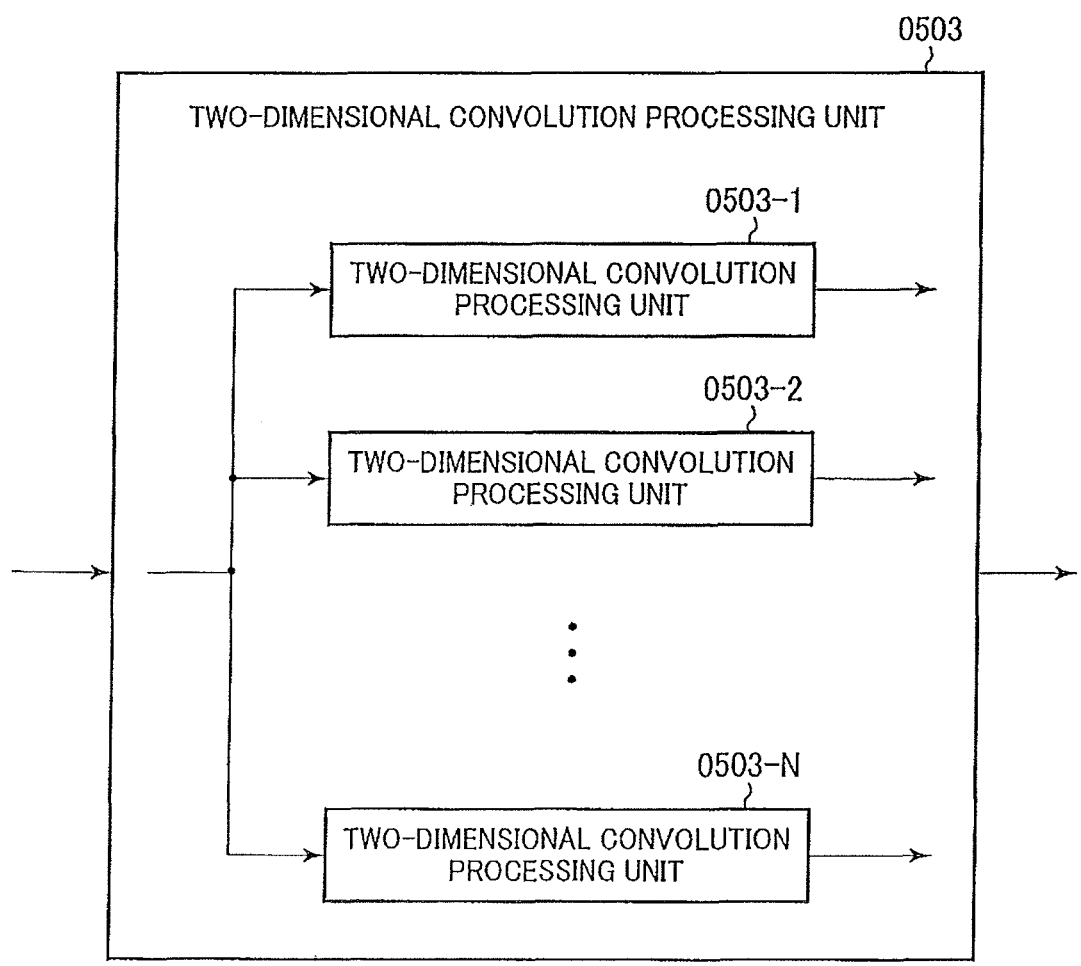
FIG. 14 is a block diagram illustrating a two-dimensional convolution processing unit according to another modification example of the present embodiment.

Next, description will be given of another modification example of the present embodiment, using FIG. 14. FIG. 14 is a block diagram illustrating the other modification example of the present embodiment. As illustrated in FIG. 14, the two-dimensional convolution processing unit 0503 of the ultrasound diagnostic apparatus 0001 includes two or more two-dimensional convolution processing units. The two-dimensional convolution processing units 0503 (0503-1 to 0503-N) receive light source slice data from the light source data holding unit 0502, each output different two-dimensional convolution data for the light source slice data (light source data), and each output the different two-dimensional convolution data to the weighted addition unit 0504. In this case, the weighted addition unit 0504 receives the light source slice data read from the light source data holding unit 0502 and the plurality of two-dimensional convolution data created by the two-dimensional convolution processing units 0503 (0503-1 to 0503-N), outputs illuminance slice data by conducting weighted addition processing of the light source slice data and the plurality of two-dimensional convolution data, and stores the illuminance slice data in the illuminance slice data storage unit 0501. In this case, the weight coefficients in the weighted addition unit 0504 hold coefficients for the light source slice data and the plurality of two-dimensional convolution data. For each output result of the two-dimensional convolution processing units 0503 (0503-1 to 0503-N), a different weight coefficient may be referred to from the two-dimensional table, and be used in the weighted addition unit 0504.

According to the modification example illustrated in FIG. 14, since the ultrasound diagnostic apparatus 0001 includes the plurality of two-dimensional convolution processing units 0503-1 to 0503-N, a plurality of shading effects corresponding to a behavior of light can be expressed, and a cross-section image in which illuminance based on a natural behavior of light (e.g., scattering) is calculated can be created. Note that the plurality of two-dimensional convolution processing units 0503-1 to 0503-N may be applied to the modification example illustrated in FIG. 13.

INDUSTRIAL APPLICABILITY

The ultrasound diagnostic apparatus of the present invention provides an arbitrary cross-section image of a three-dimensional space with an optical property (or a shading effect) indicating a behavior of light (leakage, absorption, scattering, reflection, etc.) and has effects that a cross-section image in which a structure can be clearly seen and reality is improved can be obtained, and is useful as an ultrasound diagnostic apparatus for generating a two-dimensional cross-section image from ultrasonic intensity volume data.

REFERENCE SIGNS LIST

0001 ultrasound diagnostic apparatus
0002 ultrasonic probe
0003 control unit
0004 operation unit
0005 sending unit
0006 receiving unit 0007 sending/receiving control unit
0008 beamformer unit
0009 display unit
0011 cross-section region information calculation unit
0012 three-dimensional data storage unit
0013 arbitrary cross-section image creation unit
0014 three-dimensional coordinate transformation unit
0015 volume data storage unit
0016 three-dimensional image processing unit
0017 image composition unit
0018 projection processing unit
0019 gradient calculation unit
0020 arbitrary cross-section image storage unit
0021 cross-section image processing unit
0031 light source information setting unit
0032 optical property setting unit
0033 illuminance slice data creation unit
0034 composition unit
0501 illuminance slice data storage unit
0502 light source data holding unit
0503 two-dimensional convolution processing unit
0504 weighted addition unit
1002 cross-section image setting frame
1105 cross-section image setting mark
1108 point mark of intersection
1302 cross-section image setting line
1401 weight multiplication unit
1402 addition unit

The invention claimed is:

1. An ultrasound diagnostic apparatus for use with tissue, the ultrasound diagnostic apparatus comprising:
    a light source configured to irradiate the tissue with light; and
    a processor programmed to:
        set light source data indicating a property of the light irradiated to a cross section region of the tissue;
        set a weight coefficient calculated based on a wavelength and illumination slice of the light source, the weight coefficient reflecting a behavior of the light irradiated in the tissue, the cross-section region data including intensity information on the cross-section region;
        calculate an illuminance at positions corresponding to coordinates of a plurality of cross-section regions based on the light source data and the weight coefficient, by calculating two-dimensional convolution of the light source data to generate two-dimensional convolution data;
        calculate illuminance slice data of the plurality of the cross-section regions based on the calculated illuminance by calculating weighted addition of the light source data and the two-dimensional convolution data based on the weight coefficient to create the illuminance slice data; and
        composite a two-dimensional cross-section image of the tissue from a plurality of the calculated illuminance slice data.

2. The ultrasound diagnostic apparatus according to claim 1, the processor further comprising:
    holding, as light source slice data, an initial value of the light source data and a calculated result of the weighted addition, and
    while switching the cross-section region data from an illuminance calculation starting slice to an illuminance calculation ending slice in the cross-section region data, the processor calculates two-dimensional convolution of the light source slice data to generate two-dimensional convolution data, and calculates weighted addition of the light source slice data and the two-dimensional convolution data based on the weight coefficient to calculate the illuminance slice data.

3. The ultrasound diagnostic apparatus according to claim 1, wherein the processor changes an order from the illuminance calculation starting slice to the illuminance calculation ending slice, based on a visual line direction.

4. The ultrasound diagnostic apparatus according to claim 1, wherein the processor sets the weight coefficient depending on intensity of the cross-section region data and the number of slices of the cross-section region data in which effective intensity continues in a prescribed direction.

5. The ultrasound diagnostic apparatus according to claim 1, wherein the processor includes at least one of: (i) averaging illuminance values of a plurality of the illuminance slice data, (ii) weighted addition of a plurality of the slice data, and (iii) rendering processing by an opacity table referred to by the intensity information of the cross-section region data, to composite the two-dimensional cross-section image.

6. The ultrasound diagnostic apparatus according to claim 1, further comprising:
    a display configured to display the two-dimensional cross-section image, wherein the display displays a cross-section image of the cross section region and the two-dimensional cross-section image corresponding to the cross-section image of the cross section region, in parallel.

7. An ultrasound diagnostic apparatus for use with tissue, the ultrasound diagnostic apparatus comprising:
    a light source configured to irradiate the tissue with light;
    a processor programmed to:
        set light source data indicating a property of the light irradiated to a cross section region of the tissue,
        set a weight coefficient calculated based on a wavelength and illumination slice of the light source, the weight coefficient reflecting a behavior of the light irradiated in the tissue, the cross-section region data including intensity information on the cross-section region,
        calculate an illuminance at positions corresponding to coordinates of a plurality of cross-section regions based on the light source data and the weight coefficient, and calculate illuminance slice data of the plurality of the cross-section regions based on the calculated illuminance, and
        composite a two-dimensional cross-section image of the tissue from a plurality of the calculated illuminance slice data; and
    a display configured to display the two-dimensional cross-section image, wherein the display displays at least one or a combination of two or more of:
        setting a width of a region in a visual line direction for setting the plurality of cross-section regions,
        setting an arbitrary thickness in a normal direction of the cross-section region data,
        setting the number of slices of the cross-section region data,
        setting an illumination direction of the light source,
        changing a follow direction or an opposite direction of a viewpoint, and
        setting a composition method.

8. The ultrasound diagnostic apparatus according to claim 7, wherein the display displays at least one of:
    the two-dimensional cross-section image corresponding to a cross-section image of the cross section, the two-dimensional cross-section image perpendicular to the cross-section image,
a plurality of the two-dimensional cross-section images perpendicular to one another in a three-dimensional space, and
a plurality of the two-dimensional cross-section images perpendicular to the cross-section image and parallel to one another.

9. The ultrasound diagnostic apparatus according to claim 8, wherein the display:
in the case of displaying the two-dimensional cross-section image perpendicular to the cross-section image, displays a cross-section image setting frame specifying positions of the plurality of the cross-section regions for creating the plurality of the illuminance slice data,
in the case of displaying a plurality of the two-dimensional cross-section images perpendicular to one another in the three-dimensional space, displays a point mark of intersection, the point mark of intersection being a common point of intersection, and
in the case of displaying the plurality of the two-dimensional cross-section images perpendicular to the cross-section image and parallel to one another, displays a cross-section image setting line specifying positions of the cross-section regions corresponding to the plurality of two-dimensional cross-section images.

* * * * *